United States Patent
Lefler et al.

(10) Patent No.: US 10,772,837 B2
(45) Date of Patent: Sep. 15, 2020

(54) MODIFIED RELEASE MULTI-LAYER TABLET CANNABINOID FORMULATIONS

(71) Applicant: CannTab Therapeutics, Limited, Toronto (CA)

(72) Inventors: Robert Scott Lefler, Brantford (CA); Jeff Renwick, Thornhill (CA); Joshi Laxminaraya, Ajax (CA)

(73) Assignee: CannTab Therapeutics, Ltd, Toronto, Ontario (CA)

( * ) Notice: Subject to any disclaimer, the term of this patent is extended or adjusted under 35 U.S.C. 154(b) by 0 days.

(21) Appl. No.: 15/921,651

(22) Filed: Mar. 15, 2018

(65) Prior Publication Data

US 2018/0263913 A1    Sep. 20, 2018

Related U.S. Application Data

(60) Provisional application No. 62/502,628, filed on May 6, 2017, provisional application No. 62/472,159, filed on Mar. 16, 2017.

(51) Int. Cl.

| | |
|---|---|
| *A61K 9/24* | (2006.01) |
| *A61P 25/30* | (2006.01) |
| *A61K 9/20* | (2006.01) |
| *A61K 31/05* | (2006.01) |
| *A61K 31/135* | (2006.01) |
| *A61K 31/352* | (2006.01) |
| *A61K 31/4045* | (2006.01) |
| *A61K 36/185* | (2006.01) |
| *A61K 36/28* | (2006.01) |
| *A61K 36/41* | (2006.01) |
| *A61K 36/539* | (2006.01) |

(52) U.S. Cl.
CPC .............. *A61K 9/209* (2013.01); *A61K 9/205* (2013.01); *A61K 9/2013* (2013.01); *A61K 9/2059* (2013.01); *A61K 9/2068* (2013.01); *A61K 31/05* (2013.01); *A61K 31/135* (2013.01); *A61K 31/352* (2013.01); *A61K 31/4045* (2013.01); *A61K 36/185* (2013.01); *A61K 36/28* (2013.01); *A61K 36/41* (2013.01); *A61K 36/539* (2013.01); *A61P 25/30* (2018.01); *A61K 9/2018* (2013.01); *A61K 9/2027* (2013.01); *A61K 9/2031* (2013.01); *A61K 9/2054* (2013.01)

(58) Field of Classification Search
None
See application file for complete search history.

(56) References Cited

U.S. PATENT DOCUMENTS

| | | | | |
|---|---|---|---|---|
| 2011/0117216 | A1* | 5/2011 | Velasco Diez | A61K 31/05 424/725 |
| 2012/0231083 | A1* | 9/2012 | Carley | A61K 9/0095 424/494 |

OTHER PUBLICATIONS

Hammad Tawhidul Haque Nutan's dissertation (Hereafter, Hammad, Texas Tech University Health Science Center, 2004).*

(Continued)

*Primary Examiner* — Bong-Sook Baek

(57) ABSTRACT

The present invention provides modified release pharmaceutical compositions, and methods for administering the compositions to a user, including humans. The composition may contain a combination of ingredients in proportions calculated to achieve therapeutic effect, including at least the following ingredients: one or more natural or synthetic cannabinoids, one or more release modifying agent(s), and one or more pharmaceutically acceptable excipient(s). The composition may be in a multi-layered solid dosage form to provide fast, controlled and also sustained release of specific ingredients. More specifically, the invention relates to modified release pharmaceutical compositions comprising cannabinoids and a process for preparation thereof. More specifically, the invention may control drug release in accordance with the therapeutic purpose and pharmacological properties of active substances.

10 Claims, No Drawings

(56) References Cited

OTHER PUBLICATIONS

Wikipedia entry "http://en.wikipedia.org/wiki/Tetrahydrocannabinol", accessed May 25, 2015.
G.W. Pharmaceuticals: Products and Pipeline. accessed at: "https://www.gwpharm.com/products-pipeline/sativex" accessed on Mar. 5, 2017).
Novartis: Press release Mar. 30, 2009. Available at: http://www.novartis. com/, accessed Mar. 5, 2017.
Why Marinol® is Not as Good as Real Marijuana, posted by Johnny Green on Mar. 5, 2012, "http://www.theweedblog.com/why-marinol-is-not-as-good-as-real-marijuana", incorporated in its entirety accessed Mar. 5, 2017).
The Pharma Innovation vol. 1 No. 7 2012 "www.thepharmajournal.com" Page | 116 Osmotic-Controlled Release Oral Delivery System: An Advanced Oral Delivery Form. Nitika Ahuja, Vikash Kumar, Permender Rathee. Accessed Mar. 5, 2017.
www.gattefosse.com. Accessed Mar. 5, 2017.
en.wikipedia.org/wiki/Microcrystalline_cellulose. Accessed Sep. 16, 2016.
Dave RH. Overview of pharmaceutical excipients used in tablets and capsules. Drug Topics (online). Advanstar. Oct. 24, 2008 http://drugtopics.modernmedicine.com/drugtopics/Top+News/Overview-of-pharmaceutical-excipients-used-in-tabl/ArticleStandard/Article/detail/561047. Accessed Mar. 5, 2017.
Poly acrylic acid; wisegeek.com Accessed Mar. 5, 2017.
Polyacrylic acid; wikipedia.com Accessed Mar. 5, 2017.
Shojaee et al., An Investigation on the Effect of Polyethylene Oxide Concentration and Particle Size in Modulating Theophylline Release from Tablet Matrices; AAPS PharmSciTech, vol. 16, No. 6, Dec. 2015.
David A Bender. Starch, Pregelatinized. A Dictionary of Food and Nutrition. 2005. Retrieved from Encyclopedia.com.
Dow Industries—Polyox Water-Soluble Resins in Pharmaceutical Applications, (2004).

\* cited by examiner

MODIFIED RELEASE MULTI-LAYER TABLET CANNABINOID FORMULATIONS

The present application claims priority from provisional patent application 62/502,628, entitled "Modified Release Multi-Layer Tablet Cannabinoid Formulations" filed May 6, 2017, and provisional patent application 62/472,159, entitled "Modified Release Multi-Layer Tablet Cannabinoid Formulations" filed Mar. 16, 2017.

FIELD OF THE INVENTION

The present invention pertains to the field of modified release pharmaceutical compositions of one or more natural or synthetic cannabinoids, and its use, for example, in pharmaceutical and nutraceutical indications.

BACKGROUND OF THE INVENTION

The identification of cannabidiol (CBD) and delta-9-tetrahydrocannabinol (THC) as the active compounds of marijuana (Cannabis sativa) prompted extensive research in medicinal chemistry and the development of numerous cannabinoid analogs, a class of diverse terpenophenols derived from Cannabis sativa and synthetic chemical compounds, that interact with cannabinoid receptors on cells and repress neurotransmitter release in the brain (Appendino G, Chianese G, Taglialatela-Scalfati O, Cannabinoids: occurrence and medicinal chemistry. Curr Med Chem 2011; 18: 1085-99; Massi P, Solinas M, Cinqina V, Parolaro D. Cannabidiol as potential anticancer drug. Br J Clin Pharmacol (2013) 75(2): 303-312).

The most notable cannabinoid is the phytocannabinoid tetrahydrocannabinol (THC), the primary psychoactive component of Cannabis sativa. Cannabidiol (CBD) is another major constituent of the plant. From Wikipedia, en.wikipedia.org/wiki/Tetrahydrocannabinol which was accessed May 25, 2015. All or any of these cannabinoids can be used in the present invention.

Synthetic cannabinoids encompass a variety of distinct chemical classes: the cannabinoids structurally related to THC, the cannabinoids not related to THC, such as (cannabimimetics) including the aminoalkylindoles, 1,5-diarylpyrazoles, quinolines, and arylsulfonamides, and eicosanoids related to the endocannabinoids. All or any of these cannabinoids can be used in the present invention.

Delta-9-tetrahydrocannabinol (dronabinol) is a naturally occurring compound and is the primary active ingredient in marijuana. Marijuana is dried hemp plant Cannabis sativa. The leaves and stems of the plant contain cannabinoid compounds (including dronabinol). Dronabinol has been approved by the Food and Drug Administration for the control of nausea and vomiting associated with chemotherapy and for appetite stimulation of patients suffering from wasting syndrome. Synthetic dronabinol is a recognized pharmaceutically active ingredient (API), but natural botanical sources of Cannabis rather than synthetic THC are also known in the art. All or any of these cannabinoids can be used in the present invention.

Dronabinol is the international nonproprietary name for a pure isomer of THC, (−)-trans-Δ9-tetrahydrocannabinol, which is the main isomer, and the principal psychoactive constituent, found in Cannabis. Synthesized dronabinol is marketed as Marinol® (a registered trademark of Solvay Pharmaceuticals).

Dronabinol is a light yellow resinous oil that is sticky at room temperature and hardens upon refrigeration. Dronabinol is insoluble in water and is formulated in sesame oil. It has a pKa of 10.6 and an octanol-water partition coefficient: 6,000:1 at pH 7. After oral administration, dronabinol has an onset of action of approximately 0.5 to 1 hours and peak effect at 2 to 4 hours. Duration of action for psychoactive effects is 4 to 6 hours, but the appetite stimulant effect of dronabinol may continue for 24 hours or longer after administration.

CBD does not have the clinically undesirable (but recreationally desirable) psychotropic effects, but is capable of inhibiting many effects of receptor ligands in the endocannabinoid system, which are responsible for the expression of THC's angiogenic and psychotogenic properties (Zuardi A W. Cannabidiol: from an inactive cannabinoid to a drug with wide spectrm of action. Rev Bras Psiquiatr 30: 271-280). Despite its different pharmacological and behavioural effects, CBD shares many beneficial effects, including the capacity to act as an immunomodulator, with 'classic' psychocannabinoids (Kozela E, Lev N, et al. Cannabidiol has been shown to inhibit pathogenic T cells, decreases spinal microglial activation and ameliorates multiple sclerosis-like disease in C57BL/6 mice. (2011) Br J Pharmacol 163: 1507-1519).

Anti-Inflammatory Activities

Cannabis extracts and several cannabinoids have been shown to exert broad anti-inflammatory activities in experimental models of inflammatory central nervous system (CNS) degenerative diseases. While clinical use of many cannabinoids is limited by their psychotropic effects, phytocannabinoids like CBD, which are devoid of psychoactive activity, are potentially safe and therapeutically effective alternatives for the alleviation of neuroinflammation and neurodegeneration (Kozela E, Lev N, et al. Cannabidiol inhibits pathogenic T cells, decreases spinal microglial activation and ameliorates multiple sclerosis-like disease in C57BL/6 mice. (2011) Br J Pharmacol 163: 1507-1519).

CBD exerts a wide range of anti-inflammatory properties and regulates cell cycle and function of various immune cells. These effects include suppression of humoral responses, such as release of cytokines, chemokines, growth factors, as well as suppression of immune cell proliferation, activation, maturation, migration, and antigen presentation (Mechoulam et al., Cannabidiol—recent advances. (2007) Chem Biodivers 4: 1678-1692).

Among the many types of neurodegenerative diseases in which inflammation is involved, multiple sclerosis (MS) is one of those clearly induced and driven by dysfunctional immune system activity. MS is a demyelinating disease which causes cytotoxic, degenerative processes, including inflammation, demyelination, oligodendrocyte cell death, and axonal degeneration. (Ribeiro R, Yu F, et al. This leads to neurological deficits and clinical symptoms of visual and sensory disturbances, motor weakness, tremor, ataxia, and progressive disability (Compston A, Coles A. Multiple sclerosis. (2008) Lancet 372: 1502-1517). There is currently no cure.

The endocannabinoid system has emerged as a promising therapeutic target for MS (Ribeiro R, Yu F, et al. Therapeutic potential of a novel cannabinoid agent C52 in the mouse model of experimental autoimmune encephalomyelitis. (2013) Neuroscience 254: 427-442). Several cannabinoids, including THC and CBD, exhibit anti-proliferative, antioxidative, and neuroprotective properties (Mechoulam R, Peters M, Murillo-Rodriguez E, et al. Cannabidiol—recent advances. (2007) Chem Biodivers 4: 1678-1692). Sativex® (GW Pharmaceuticals), the world's first pharmaceutical prescription medicine derived from the Cannabis plant, was launched in April 2005 for neuropathic pain relief in multiple sclerosis. It is a mixture of CBD and donabinol, and was most recently formulated as an oromucosal spray for the treatment of symptoms of spasticity associated with multiple sclerosis (G. W. Pharmaceuticals: Products and Pipeline. accessed at: www.gwpharm.com/products-pipeline/sativex on Mar. 5, 2017).

Most current MS therapies are directed against various immune cells to achieve immunosuppressive effects, but immunosuppression alone is insufficient for therapeutic effect, especially in late, secondary, progressive MS, where neurodegenerative processes become resistant to immunomodulation (Bennett J L, Stuve O. Update on inflammation neurodegeneration and immunoregulation in multiple sclerosis: therapeutic implications. Clin Neuropharmacol 32: 121-132).

It appears that in this unique aspect, the endocannabinoid system could provide a rescue mechanism, particularly for patients suffering from late-stage MS. Research indicates that THC-like cannabinoids possess ameliorating, neuroprotective activity in this respect, and that cannabinoid-mediated neuroprotection, rather than immunosuppression, is relevant for the recovery process at the later, remissive stages of MS (Croxford J L, Pryce G, et al. Cannabinoid-mediated neuroprotection, not immunosuppression, may be more relevant to multiple sclerosis. J Neuroimmunol (2008) 193: 120-129; Maresz K. Pryce G et al. Direct suppression of CNS autoimmune inflammation via the cannabinoid receptor CB1 on neurons and CB2 on autoreactive T cells. (2007) Nat Med 13: 492-497).

Cancer

Several studies have demonstrated that cannabinoids exert an inhibitory action on the proliferation of various cancer cell lines, and are able to slow down or arrest the growth of different models of tumour xenograft in experimental animals (Alexander A, Smith P F, Rosengren R J. Cannabinoids in the treatment of cancer. Cancer Lett 285: 6-12); Flygare J, Sander B. The endocannabinoid system in cancer-potential therapeutic target? Semin Cancer Biol 18: 176-189; Freimuth N, Ramer R, Hinz B, Antitumorogenic effects of cannabinoids beyond apoptosis. (2010) J Pharmacol Exp Ther 332: 336-344; Guindon J, Hohmann A G. The endocannabinoid system and cancer: therapeutic implication. (2011) Br J Pharmacol 163: 1447-1463). These data have attracted increasing interest for clinical exploitation of cannabinoid-based anti-cancer therapies.

Cannabinoids are currently used in cancer patients to palliate wasting, emesis, and pain that often accompany cancer (Massi P, Solinas M, Cinqina V, Parolaro D. Cannabidiol as potential anticancer drug. *Br J Clin Pharmacol* (2013) 75(2): 303-312). A shortcoming for these and forthcoming indications clearly lies in the psychoactive adverse effects of cannabinoids, resulting in increased interest in the non-psychoactive cannabinoid CBD in recent years (Ramer R, Merkord J, et al. Cannabidiol inhibits cancer cell invasion via upregulation of tissue inhibitor of matrix metalloproteinases-1. (2010) Biochem Pharm 79: 955-966).

Meanwhile, a formulation including a 1:1 ratio of THC to CBD has been approved for pharmacotherapy of multiple sclerosis-related spasticity and pain in Canada (Wade D T, Makela P, et al. Do *Cannabis*-based medicinal extracts have general or specific effects on symptoms in multiple sclerosis? (2004) Mult Scler 10: 434-41). Further formulations and indications are needed; modulation of cancer cell invasion has recently emerged as a topic of increasing interest (McAllister S D, Christian R T, et al. Cannabidiol as a novel inhibitor of id-1 gene expression in aggressive breast cancer cells. Mol Cancer Ther 2007; 6:2921-7; Blazquez C, Salazar M, et al. Cannabinoids inhibit glioma cell invasion by down-regulating matrix metalloproteinase-2 expression. (2008) Cancer Res 68: 1945-52; Ramer R, Hinz B. Inhibition of cancer cell invasion by cannabinoids via increased expression of tissue inhibitor of matrix metalloproteinases-1. (2008) J Natl Cancer Inst 100: 59-69).

Several cannabinoids have been shown to exert antiproliferative and pro-apoptotic effects in various cancer types (lung, glioma, thyroid, lymphoma, skin, pancreas, uterus, breast, prostate, and colorectal carcinoma) (D. Wade, P. Robson, H. House, et al., Clin. Rehabil. 17 (2003) 21e29; T. J. Nurmikko, M. G. Serpell, B. Hoggart, et al., Pain 133 (2007) 210e220; J. R. Johnson, M. Burnell-Nugent, D. Lossignol, et al., J. Pain Symptom Manage. 39 (2010) 167e1799; M. C. McCowen, M. E. Callender, J. F. Lawlis, Science 113 (1951) 202e203; F. Lantemier, D. Boutboul, J. Menotti, et al., Transpl. Infect. Dis. 11 (2009) 83e88; J. Breedt, J. Teras, J. Gardovskis, et al., Antimicrob. Agents Chemother. 49 (2005) 4658e4666). Other antitumourogenic mechanisms are emerging, showing their ability to interfere with tumour neovascularization, cancer cell migration, adhesion, invasion and metastasization (McGivem J G, Neuropsychiatr Dis. Treat. 3 (2007) 69-85).

The clinical use of THC and additional synthetic agonists is often limited by their unwanted psychoactive side effects, and for this reason, interest in non-psychoactive phytocannabinoids, such as CBD, has substantially increased in recent years. CBD does not have psychotropic activity and yet maintains very high potency. In 2006, CBD was used to selectively inhibit the growth of different breast tumour cell lines (MCF7, MDA-MB-231), while exhibiting lower potency in non-cancer cells (Ligresti A, Moriello A S, Starowicz K, Matias I, Pisanti S, De Petrocellis L, Laezza C, Portella G, Bifulco M, Di Marzo V, Antitumor activity of plant cannabinoids with emphasis on the effect of cannabidiol on human breast carcinoma. J Pharmacol Exp Ther 2006; 318: 1375-87).

CBD also possesses antitumoural properties in gliomas, tumours of glial origin characterized by a high morphological and genetic heterogeneity and considered one of the most devastating neoplasms, showing high proliferative rate, aggressive invasiveness and insensitivity to radio- and chemo-therapy (Massi P, Solinas M, Cinqina V, Parolaro D. Cannabidiol as potential anticancer drug. *Br J Clin Pharmacol* (2013) 75(2): 303-312). Research findings have also suggested a novel mechanism underlying the anti-invasive action of CBD on human lung cancer cells, and imply its use as a therapeutic option for the treatment of invasive cancers, as well as leukemia (S. Goodin, Am. J. Health-Syst Pharm. 65 (2008) S10eS15; F. Y. F. Lee, R. Borzilleri, C. R. Fairchild, et al., Cancer Chemother. Pharmacol. 63 (2008) 157e166; A. Conlin, M. Fornier, C. Hudis, et al., Eur. J. Cancer 44 (2008) 341e352; D. R. P. Guay, Consult Pharm. 24 (2009) 210e226; N. Slatkin, J. Thomas, A. G. Lipman, et al., J. Support Oncol. 7 (2009) 39e46; F. M. Reichle, P. F. Conzen, Curr. Opin. Invest. Drugs 9 (2008) 90e100; C. S. Yuan, Ann. Pharmacother. 41 (2007) 984e993; M. D. Kraft, Am. J. Health Syst. Pharm. 64 (2007) S13eS20; Novartis: Press release 30 Mar. 2009. Available at: www.novartis.com/ accessed Mar. 5, 2017; D. L. Higgins, R. Chang, D. V. Debabov, et al., Antimicrob. Agents Chemother. 49 (2005) 1127e1134; J. K. Judice, J. L. Pace, Bioorg. Med. Chem. Lett. 13 (2003) 4165e4168; S. Avaleeson, J. L. Kuti, D. P. Nicolau, Expert Opin. Invest. Drugs 16 (2007) 347e357).

In addition to their anti-proliferative and pro-apoptotic actions, it has been shown that cannabinoids can affect other important processes in tumourigenesis, in particular, angiogenesis, or the formation of new blood vessels from pre-existing ones—an essential step in tumour growth, invasion, and metastasis and a major therapeutic target for cancer therapy (Solinas M, Massi P, Cantelmo A R, et al. Cannabidiol inhibits angiogenesis by multiple mechanisms. Brit J Pharmacol (2012) 167: 1218-31). Strategic approaches are needed that are aimed at the timely administration of natural, non-psychotropic cannabinoids (such as CBD) that are able to suppress pro-angiogenic factor production while binding with low affinity to cannabinoid receptors, thereby excluding psychotropic and immune or peripheral effects (Casanova M L, Blazquez C et al. Inhibition of skin tumor growth and angiogenesis in vivo by activation of cannabinoid receptors. J Clin Invest 111: 43-50; Blazquez C, Gonzales Feria L, Alvarez L, et al. Cannabinoids inhibit the vascular endothelial growth factor pathway in gliomas. Cancer Res 64: 5617-5623; Gertsch J, Pertwee R G, Di Marzo V, Phytocannabinoids beyond the *Cannabis* plant—do they exist? (2010) Br J Pharmacol 160: 523-29; Preet A, Ganju R K, Groopman J E. Delta-9-tetrahydrocannabinol inhibits epithelial growth factor-induced lung cancer cell migration in vitro as well as its growth and metastasis in vivo. (2008) Oncogene 27: 339-346; Russo E B. Taming THC: potential *Cannabis* synergy and phytocannabinoid-terpenoid entourage effects. (2011) Br J Pharmacol 163: 1344-1364).

Collectively, the non-psychoactive plant-derived cannabinoid CBD exhibits pro-apoptotic and anti-proliferative actions in different types of tumours and may also exert anti-migratory, anti-invasive, anti-metastatic, and perhaps anti-angiogenic properties. On this basis, evidence supports that CBD is a potent and selective inhibitor of cancer cell growth and spread (Massi P, Solinas M, Cinqina V, Parolaro D. Cannabidiol as potential anticancer drug. Br J Clin Pharmacol (2013) 75(2): 303-312). Considering its demonstrated clinical efficacy and safety in multiple sclerosis patients, the findings suggest that CBD is worthy of clinical consideration in an appropriate formulation for cancer therapy.

Mental Illness/Neuropathic Pain

Spinal cord injury and neuropathic pain are diseases in which alterations in the endocannabinoid system have been demonstrated, paving the way for new therapeutic strategies in which normal endocannabinoid system functionality is restored (Pacher P, Batkai S, Junos G. The endocannabinoid system as an emerging target of pharmacotherapy. Pharmacol Rev 2006; 58: 389-462).

Sativex® was also approved for use in some countries as an adjunctive analgesic for severe pain in advanced cancer patients, reducing use of, and dependency on, opioid medications. It efficiently reduces pain in patients with advance cancer, and has been recommended by the FDA for direct entry into Phase III trials (Johnson J R, Burnell-Nugent M, Lossignol D, et al. J. Pain Symptom Manage. 39 (2010) 167-79).

Many studies present evidence that support the therapeutic potential of cannabidiol to mitigate the detrimental and psychotogenic effects of delta-9-tetrahydrocannabinol, mitigating its effects of acute induction of psychotic and anxiety systems (Bhattacharyya S, Morrison P D, Fusar-Poli P, et al. Opposite effects of THC and CBD on human brain function and psychopathology. *Neuropsychopharmacol.* 2009; 35: 764-774; Hagerty S L, Williams S L, Mittal V A, Hutchison K E, The *Cannabis* conundrum: Thinking outside the THC box. *J Clin Pharmacol.* 2015 August; 55(*): 839-41).

Where THC has anxiogenic effects, CBD reduces subjective anxiety, achieving clinically significant reductions in anxiety, cognitive impairment, and discomfort. (Fusar-Poli P, Crippa J A, Bhattacharyya S, et al. Distinct effects of delta-9-tetrahydrocannabinol and cannabidiol on neural activation during emotional processing. *Arch Gen Psychiat.* 2009; 66: 95-105; Bergamaschi M M, Queiroz R H C, Chaga M H N, et al. Cannabidiol reduces the anxiety induced by simulated public speaking in treatment-naïve social phobia patients. Neuropsychopharmacol. 2011; 36: 1219-1226.). Evidently, the effects of *Cannabis* are complex and arise from myriad cannabinoids; they are distinct from the artificially uniform effect of THC alone. The therapeutic effects of these cannabinoids can be harnessed most effectively through formulations which, as with the present invention, account for the complexity of cannabinoids and their interactions, and the mechanisms that underlie different effects of use in humans (i.e., cognitive effects versus anxiolytic or anxiogenic effects) (Hagerty S L, Williams S L, Mittal V A, Hutchison K E, The *Cannabis* conundrum: Thinking outside the THC box. J Clin Pharmacol. 2015 August; 55(*): 839-41).

Epilepsy

Epilepsy is a prevalent and devastating disorder of the CNS, which may be defined as a brain condition causing spontaneous recurrent seizures. These seizures are sometimes both progressively severe and accompanied by cognitive and behavioural comorbidities (Goldberg E M, Coulter D A. Mechanisms of epileptogenesis: a convergence on neural circuit dysfunction. Nat. Rev. Neurosci. 14 (2013) 337-49).

Epileptogenesis (latency period) refers to a scantily understood cascade of events that generally transmute a non-epileptic brain into one that triggers spontaneous seizures; these events occur in a specific time window included between a brain-damaging insult such as stroke, infection, or genetic predisposition, and the onset of unprovoked and unpredictable seizures (Ibid.) During this period, a specific treatment may stop or modify the epileptogenic process and thereby positively influence the quality of life of an epileptogenic subject (White H S, Loscher W. Searching for the ideal epileptogenic agent in experimental models: single treatment versus combinatorial treatment strategies. (2014) Neurotherapeutics 11: 373-384; Citraro R, Leo A, et al. Antidepressants but not antipsychotics have antiepileptogenic effects with limited effects on comorbid depressive-like behavior in the wag/rij rat model of absence epilepsy. (2015) Br J Pharmacol 172: 3177-3188).

Currently, among the major unmet needs in the treatment of epilepsy there is the identification of disease-modifying drugs that can completely prevent epilepsy or slow its progression (Leo A, Russo E, Elia M. Cannabidiol and epilepsy: rationale and therapeutic potential. (2016) Pharma Res 107: 85-92). Unfortunately, many new antiepileptic drugs (AEDs) as well as older AEDs present solely symptomatic features, and do not possess antiepileptogenic or disease modifying features, and show several negative side effects influencing quality of life as much as seizures (Kwan P, Brodie M J, Refractory epilepsy: mechanisms and solutions. (2006) Expert Rev Neurother 6: 397-406; Perucca P, Gilliam F G, Adverse effects of antiepileptic drugs, (2012) Lancet Neurol 11: 792-802).

Emphasis has been placed on phytocannabinoids, which has demonstrated clinically significant antiseizure effects in clinical trials (Reddy D S, Golub V, The pharmacological basis of *Cannabis* therapy for epilepsy, J Pharmacol Exp Ther (2016) 45-55). Anecdotal reports indicate mixed findings for seizure prevalence subsequent to administration of THC, however, where a greater prevalence of grand mal seizures may be observed subsequent to consumption in previously seizure-free patients (Ramsey H H, Davis J P. Anti-epileptic action of marijuana-active substances, Fed Proc 8 (1949), 67; Consroe P F, Wood G C, Buchsbaum H. Anticonvulsant nature of marihuana smoking. JAMA (1975) 234: 306-307; Ellison J M, Gelwan E, Ogletree J. Complex partial seizure symptoms affected by marijuana abuse. J Clin. Psychiatry (1990) 51: 439-440; Keeler M H, Reifler C B. Grand mal convulsions subsequent to marijuana use. Case report. Dis. Nerv. Syst. (1967) 28: 474-75).

Rather than a "blunt instrument" approach to administration of medical *Cannabis*, these studies of epileptic sujects suggest the need for highly nuanced formulations which account for the varying properties of each substituent cannaboid(s), and account for the desired pharmacokinetics of each based on the desired therapeutic effect sought to be achieved in the patient. The present invention affords such a nuanced mechanism of action, over and above the existing art in this field.

Studies have also suggested that desired therapeutic effects can be achieved via administration of pure CBD in twice-daily dosages in paediatric patients, resulting in seizure reduction ranging from total seizure freedom to reductions of 25-80%, and the absence of deleterious side effects (Saade D, Joshi C. Pure cannabidiol in the treatment of malignant migrating partial seizures in infancy: A case report. Pediatr. Neurol. 52 (2015) 544-47; Porter B E, Jacobson C. Report of a parent survey of cannabidiol-enriched *Cannabis* use in pediatric-resistant epilepsy. Epilepsy Behav (2013) 29: 574-77). The present formulation is capable of achieving sustained therapeutic effect in a single dose, negating the cost and necessity of multiple dosages, and improving adherence, particularly in paediatric, elderly, and severely epileptic populations, where adherence is difficult and consequences are severe. As such, the present invention offers significant advantages over and above existing antiepileptic drugs (AEDs), accompanied by a superior pharmacokinetic, pharmacodynamic, and side effects profile. With demonstrated effects on cognitive performance and mood disorders, the present invention possesses the additive value of simultaneously managing psychiatric comorbidities associated with epilepsy, which are often more harmful to patients than seizures themselves (Dos Santos R G, Hallak J E, et al. Phytocannabinoids and epilepsy. J Clin Pharm Ther (2015) 40: 135-43; Scuederi C, Filippis D D, et al. Cannabidiol in medicine: a review of its therapeutic potential in cns disorders. Phytother. Res. (2009) 23: 597-602). The present invention, with its established safety profile, ease of use, and reliable evidence base of therapeutic efficacy will be of additional value for drug-resistant epilepsies which are non-responsive to conventional AEDs (Leo A, Russo E, Elia M. Cannabidiol and epilepsy: rationale and therapeutic potential. (2016) Pharma Res 107: 85-92).

Mood Disorders

High CBD intake relative to THC has been associated with lower scores on the positive dimensions of the CAPE (Community Assessment of Psychic Experiences) Scale, inhibition of psychotic symptoms, and reduced deficiencies in episodic memory (Englund A, Morrison P, et al. Cannabidiol inhibits THC-elicited paranoid symptoms and hippocampal-dependent memory impairment. J Pharmacol (2013) 27(1): 19-27). The present formulation presents the advantage of an intentional dosage of synthetic or natural preparations with ideal pharmacology, to the exclusion of other cannabinoids and their respective pharmacokinetic and pharmacodynamics influences. The "protective effects" afforded by extended or sustained release formulations can be harnessed by virtue of the present invention, along with the desired therapeutic effects of cannabidiols like CBD, either alone or in concert with therapeutically effective amounts of other cannabinoids. (Englund A, Morrison P, et al. Cannabidiol inhibits THC-elicited paranoid symptoms and hippocampal-dependent memory impairment. J Pharmacol (2013) 27(1): 19-27).

Research has also indicated that the endocannabinoid system is intricately involved in the pathophysiology of depression, with CB1 receptors widely distributed in brain areas related to affective disorders, where expression is otherwise regulated by anti-depressants (Devane W A, Dysarz F A, et al. Determination and characterization of a cannabinoid receptor in rat brain. Mol Pharmacol (1988) 34: 605-613; Hill M N, Gorzalka B B. Is there a role for the endocannabinoid system in the etiology and treatment of melancholic depression? Behav Pharmacol (2005) 16: 333-352; Hill M N, Carrier E J, et al. Regional alterations in the endocannabinoid system in an animal model of depression: effects of concurrent antidepressant treatment. *J Neurochem* (2008) 106: 2322-36).

Administration of CBD achieves characteristic effects of induced anti-psychotic and anxiolytic activity in subjects, and also attenuates the development of stress-induced behavioural consequences, raising the possibility that CBD could be useful for treating psychiatric disorders thought to involve impairment of stress-coping mechanisms, such as depression (Guimaraes F S, Chiaretti™, et al. Antianxiety effect of cannabidiol in the elevated plus-maze. Psychopharmacology (1990) 100: 558-559; Resstel L B, Joca S R, et al. Effects of cannabidiol and diazepam on behavioural and cardiovascular responses induced by contextual conditioned fear in rats. *Behav Brain Res* (2006) 172(2): 294-98; Resstel L B, Tavares R F, et al. 5-HT1A receptors are involved in the cannabidiol-induced attenuation of behavioural and cardiovascular-induced attenuation of behavioural and cardiovascular responses to acute restraint stress in rats. Br J Pharmacol (2009) 156(1): 181-88; Zuardi A W, Shirakawa I, et al. Action of cannabidiol on the anxiety and other effects produced by delta 9-THC in normal subjects. Psychopharmacology (1982) 76: 245-50).

Studies indicate that CBD has a favorable profile in a model predictive of antidepressant-like activity in comparison to prototype antidepressants, but that such effects are only attainable at precise dosages, with smaller or higher doses producing no effect (Porsolt R D, Le Pichon M, Jalfre M. Depression: a new animal model sensitive to antidepressant treatment. Nature (1977) 266: 730-32; Zanelati T V, Biojone C, et al. Antidepressant-like effects of cannabidiol in mice: possible involvement of 5-HT1A receptors. Br J Pharmacol (2010) 159: 122-28). The present invention has a formulation which is capable of administering said dosage in accordance with the most clinically appropriate pharmacokinetic and pharmacodynamic profile in order to achieve desired therapeutic effects in a patient presenting with a specific pathophysiology, such as major depressive disorder.

Sleep

Delta-9-tetrahydrocannabiniol (THC) increases sleep (Pivik, R. T., Zarcone, V., Dement, W. C. and Hollister, L. E. (1972) D-9-tetrahydrocannabinol and synhexl: effects on human sleep patterns. Clin. Pharmacol. Ther. 13 (3), 426-435; Feinberg, I., Jones, R., Walker, J. M., Cavness, C. and March, J. (1975) Effects of high dosage D-9-tetrahydrocannabinol on sleep patterns in man. Clin. Pharmacol. Ther. 17 (4), 458-466; Feinberg, I., Jones, R., Walker, J., Cavness, C. and Floyd, T. 1n (1976) Effects of marijuana extract and tetrahydrocannabinol on electroencephalographic sleep patterns. Clin. Pharmacol. Ther. 19 (6), 782-794). The chemistry of CBD has been examined, and its central nervous system (CNS) pharmacological properties, including its anticonvulsant, anxiolytic, and sedative effects, have been documented (Chesher, G. B., Jackson, D. M. and Malor, R. M. (1975) Interaction of $D^9$-tetrahydrocannabinol and cannabidiol with phenobarbitone in protecting mice from electrically induced convulsions. J. Pharm. Pharmacol. 27 (8), 608-609; Pickens, J. T. (1981) Sedative activity of *Cannabis* in relation to its $D^0$-trans-tetrahydrocannabinol and cannabidiol content. Br. J. Pharmacol. 72 (4), 649-656; Russo, E. and Guy, G. W. (2006) A tale of two cannabinoids: the therapeutic rationale for combining tetrahydrocannabinol and cannabidiol. Med. Hypotheses 66 (2), 234-246).

In studies, it has been shown that CBD improves sleep in individuals suffering from insomnia (Carlini E A, Cunha J M, Hypnotic and antiepileptic effects of cannabidiol. J. Clin. Pharmacol. 21 (suppl 8-9), 417S-427S). It has been successfully employed to block anxiety-induced REM sleep alteration via its anxiolytic effects (Hsiao Y., Yi P, et al. Effect of cannabidiol on sleep disruption induced by the repeated combination tests consisting of open field and elevated plus-maze in rats. Neuropharmacol. (2012) 62: 373-84). Other studies have exhibited clinically significant improvements in sleep in subjects suffering from post-traumatic stress-related insomnia, even when subjects received no pharmaceutical medications to treat sleep disorders aside from cannabidiol oil (Shannon S., Effectiveness of cannabidiol oil for pediatric anxiety and insomnia as part of posttraumatic stress disorder: a case report. Perm J. (2016) 20(4): 16-005). In other studies, the systemic acute administration of CBD appears to increase total sleep time in subjects, in addition to increasing sleep latency in the light period of the day of administration (Chagas M., Crippa J., et al. Effects of acute systemic administration of cannabidiol on sleep-wake cycle in rats. J. Psychopharmacol. (2013) 27(3): 312-16).

Addiction and the Endocannabinoid System

Drug addiction is a chronic, relapsing disease characterized by the compulsion to seek and take a drug, loss of control in limiting intake and emergence of negative emotional states when access to the drug is prevented (Koob and Le Moal, Drug abuse: hedonic homeostatic dysregulation (1997) Science 278: 52-58.) It is a chronic disorder involving persistent changes in the central nervous system.

Prototypical examples of those changes include tolerance, dependence, and/or sensitization after repeated drug exposure with corresponding neurochemical changes in the brain (Chao and Nestler, Molecular neurobiology of drug addiction (2004) Annu Rev Med. 55:113-132; Nestler, Molecular mechanisms of drug addiction (2004) Neuropharm. 47:24-32; Ron and Jurd, The 'ups and downs' of signaling cascades in addiction (2005) Sci STKE 309:re 14). It is these neuropharmacological and neuroadaptive mechanisms that mediate the transition from occasional, controlled drug use to the loss of behavioral control over drug-seeking and drug-taking that defines addiction.

These emotional, cognitive and behavioral effects are commonly linked to a neurobiological subtract. The endocannabinoid system is strongly implicated in these neuroadaptations, which are induced through repeated exposure to drugs of abuse (Fattore et al. Endocannabinoid system and opioid addiction: behavioral aspects (2005) Pharmacol Biochem Behav 81: 343-359). Such findings include the main legal and illegal drugs used in developed countries: nicotine, alcohol, *cannabis*, cocaine and opioids (Arnold, The role of endocannabinoid transmission in cocaine addiction (2005) Pharmacol Biochem Behav 81: 396-406; Colombo et al. Endocannabinoid system and alcohol addiction: pharmacological studies (2005) Pharmacol Biochem Behav 81: 369-380; Lopez-Moreno et al., Functional interactions between endogenous cannabinoid and opioid systems: focus on alcohol, genetics and drug-addicted behaviors (2010) Curr Drug Targets 11: 406-428; Maldonado and Berrendero, Endogenous cannabinoid and opioid systems and their role in nicotine addiction (2010) Curr Drug Targets 11: 440-449; Maldonado et al., Involvement of the endocannabinoid system in drug addiction (2006) Trends Neurosci 29: 225-232; Piomelli, The endogenous cannabinoid system and the treatment of marijuana dependence (2004) Neuropharmacology 47(Suppl 1): 359-367).

The complexity of the endocannabinoid system is reflected by its implication in many different cognitive and physiological processes. It participates in the regulation and modulation of learning and memory, food intake, nociception, motor coordination, reward processes, emotional control, and various cardiovascular and immunological processes (Ameri, The effects of cannabinoids on the brain (1999) Prog Neurobiol 58: 315-348). The participation of the endocannabinoid system in most of these functional psycho-psychological processes is explained by its strong connection to the dopaminergic system, mainly through the basal ganglia and corticolimbic brain structures (Freund et al., Differences in norepinephrine clearance cerebellar slices from low-alcohol-sensitive and high-alcohol sensitive rats (2003) Alcohol 30: 9-18).

The main excitatory and inhibitory systems of the mammalian central nervous system are under the influence of the endocannabinoid system. In the addicted individual, the imbalance in glutamatergic neurotransmission is common. It is also known that a dysregulation of excitatory signaling could lead to the relapse of drug use and cravings, supporting the notion of addictive behavior as a chronic disorder (Dackis and O'Brien, Glutamatergic agents for cocaine dependence (2003) Ann N Y Acad Sci 1003:328-345). Therefore, it is easy to understand the importance of the endocannabinoid system in the phenomenon of addiction, especially when its neuromodulation is compromised, for example, by an altered performance of receptors and cellular signaling of cannabinoid CB1 receptors (Lopez-Moreno, et al. The pharmacology of the endocannabinoid system: functional and structural interactions with other neurotransmitter systems and their repercussions in behavioral addiction (2008) Addiction Biol. 13: 160-187). The endocannabinoid system is the major player and a neurobiological mechanism underlying drug reward (Onaivi, An endocannabinoid hypothesis of drug reward and addiction (2008) 1139: 412-21). The endocannabinoid system is a modulator of dopaminergic activity in the basal ganglia, elucidating its participation in the primary rewarding effects of alcohol, opioids, nicotine, cocaine, amphetamine, cannabinoids, and benzodiazepines through the release of endocannabinoids that act as retrograde messengers to inhibit classical transmitters, including dopamine, serotonin, GABA, glutamate, acetylcholine, and norepinephrine (Onaivi, An endocannabinoid hypothesis of drug reward and addiction (2008) 1139: 412-21). The endocannabinoid system is further involved in the common mechanisms underlying relapse to drug-seeking behavior by mediating the motivational effects of drug-related environmental stimuli and drug re-exposure (Maldonado et al., Involvement of the endocannabinoid system in drug addiction (2006) Trends Neurosci 29: 225-232.) The endocannabinoid system triggers or prevents reinstatement of drug-seeking behavior (Fattore et al., An endocannabinoid mechanism in relapse to drug seeking: a review of animal studies and clinical perspectives (2007) Brain Res Rev 53: 1-16).

The perturbation of the endocannabinoid system by drugs of abuse can be ameliorated by restoring the perturbed system using cannabinoid receptor ligands. Cannabinoid receptor antagonists are useful in the reduction of drug use, in smoking cessation, and reduction in alcohol consumption, and rimonabant has been demonstrated to have antagonistic activity against disruption of cognition or reward-enhancing properties of morphine, amphetamine, cocaine, (Poncelet, Blockade of CB1 receptors by 141716 selectively antagonizes drug-induced reinstatement of exploratory behavior in gerbils (1999) Psychopharmacology 144: 144-50) ethanol, and diazepam. The blockade of the behavioral aversions by cannabinoid anatagonists after chronic administration of alcohol, cocaine, and diazepam is in agreement with data obtained during cannabinoid-induced alterations in brain dispositions of drugs of abuse that correlated with behavioral alterations in mice (Reid and Bornheim, Cannabinoid-induced alterations in brain disposition of drugs of abuse (2001). Biochem. Pharmacol. 61: 1357-1367).

As the mesolimbic dopaminergic system is implicated in the reinforcing properties of most drugs of abuse, the endocannabinoid system is a therapeutic target for individuals addicted to drugs. Mice treated with CB1 antagonists (i.e. SR141716) showed a significant reduction in self-administered alcohol consumption (Colombo et al., Suppressing effect of the cannabinoid CB1 receptor antagonist, SR 141716, on alcohol's motivational properties in alcohol-preferring rats (2004) Eur J Pharmacol 498: 119-123.), cocaine-related locomotor activity (Gerdeman et al., Context-specific reversal of cocaine sensitization by the CB1 cannabinoid receptor antagonist rimonabant (2008) Neuropsychopharmacology 33: 2747-2759.), and a reduction in the reward effects of nicotine (Cohen et al., SR141716, a central cannabinoid (CB(1)) receptor antagonist, blocks the motivational and dopamine-releasing effects of nicotine in rats (2002) Behav Pharmacol 13: 451-463.)

The inhibition of FAAH (e.g. by URB597) causes a reduction of nicotine-induced dopamine activity in the nucleus accumbens, leading to a reduction in nicotine-induced reinstatement of nicotine seeking (Forget et al., Inhibition of fatty acid amide hydrolase reduces reinstatement of nicotine seeking but not break point for nicotine self-administration—comparison with CB(1) receptor blockade (2009) Psychopharmacology (Berl) 205: 613-624.)

Thus, the endocannabinoid physiological control system is a directly important natural regulatory mechanism for reward in the brain, and also contributes to reduction in aversive consequences of abused substances, such that manipulating the endocannabinoid system can be exploited in order to treat alcohol and drug dependency, and to reduce the behavioral consequences associated with withdrawal (Onaivi, An endocannabinoid hypothesis of drug reward and addiction (2008) 1139: 412-21).

Opioid Addiction

Abuse of heroin and prescription opioids have long constituted a significant burden to society both through the direct and indirect consequences of illicit opioid use. Since the mid-1990's heroin use has experienced a resurgence, particularly among younger populations. In 2004, an estimated 3.7 million people in the United States had reported using heroin at some point in their lifetime according to data collected by the National Institute on Drug Abuse. The 2008 National Survey on Drug Use and Health determined that the number of heroin users over the age of 12 in the United States had increased dramatically from 153,000 in 2007 to 213,000 in 2008.

The high abuse liability of heroin was demonstrated in a 2004 study of drug use, which found that 67% of those that used heroin also met the criteria for abuse or dependence, a statistic markedly higher than that for other drugs of abuse such as cocaine, marijuana, or sedatives (OAS).

Heroin use, while extremely problematic, is restricted to a small percentage of the population. However, non-medical use of prescription opioids is now becoming more prevalent with rates of use rapidly increasing. The misuse or abuse of prescription drugs occurs when a person takes a prescription drug that was not prescribed or taken in one dose or for reasons other than those prescribed. Abuse of prescription drugs can produce serious health effects, including addiction. The classes of prescription drugs that are commonly abused include include oral narcotics such as hydrocodone (Vicodin), oxycodone (OxyContin), propoxyphene (Darvon), hydromorphone (Dilaudid), meperidine (Demerol) and diphenoxylate (Lomotil), and their non-medical use has increased dramatically in recent years. For example, in 1990, the number of individuals initiating abuse of prescription opioids was 573,000. By the year 2000, the number had risen to over 2.5 million according to the National Institutes of Health. In 2009, for the first time, the number of individuals initiating prescription opioid use nearly equaled that of marijuana; a previously unprecedented and alarming finding. Concurrently, emergency department visits due to complications from non-medical use of hydrocodone and oxycodone rose by 170% and 450% respectively from 1994 to 2002. Furthermore, opioid-related deaths rose by more than 300% between 1999 and 2006 (OAS, 2009).

Similarly, withdrawal from opiates, such as heroin or oral narcotics, is characterized by a host of aversive physical and emotional symptoms. High rates of relapse and limited treatment success rates for opiate addiction have prompted a search for new approaches. Research over the past decade has shed light on the influence of endocannabinoids on the opioid system. Evidence from both animal and clinical studies show an interaction between these two systems, and targeting the EC system as provided by the instant invention provides a novel intervention strategy for managing opiate dependence and withdrawal.

Opioids, such as heroin and morphine, exert their physiological and behavioral effects through specific interactions with opioid receptors (Kieffer, Opioids: first lessons from knockout mice (1999) Trends Pharmacol Sci 20:19-26; Matthes et al., Loss of morphine-induced analgesia, reward effect and withdrawal symptoms in mice lacking the mu-opioid-receptor gene (1996). Nature 383:819-823.) CB1 and μ-receptors are similarly expressed in many brain areas involved in reward processes (Herkenham et al., Characterization and localization of cannabinoid receptors in rat brain: a quantitative in vitro autoradiographic study (1991). J Neurosci 11:563-583; Matsuda et al., Localization of cannabinoid receptor mRNA in rat brain (1993). J Comp Neurol 327(4), 535-550.) These receptors share common signaling cascades (Howlett, (2002). The cannabinoid receptors. Prostaglandins Other Lipid Mediat 68-69, 619-631.) There is a functional interaction between the endogenous cannabinoid and opioid systems (Manzanares et al., Pharmacological and biochemical interactions between opioids and cannabinoids (1999). Trends Pharmacol Sci 20(7), 287-294.)

Studies have demonstrated that under certain circumstances, cannabis use can be associated with positive treatment prognosis among opioid-dependent cohorts. For example, Epstein and Preston found that cannabis abuse and dependence were predictive of decreased heroin and cocaine use during treatment (Epstein and Preston, Does cannabis use predict poor outcome for heroin-dependent patients on maintenance treatment? Past findings and more evidence against (2003) Addiction 98:269-279).

Intermittent use of cannabis was associated with a lower percentage of positive opioid relapses and improved medication compliance on naltrexone therapy (Church et al., Concurrent substance use and outcome in combined behavioral and naltrexone therapy for opiate dependence (2001) Am J Drug Alcohol Abuse 27:441-452). Similarly, associations of intermittent or occasional cannabis use with improved retention in treatment for opioid dependence have also been reported (Ellner, (1977) Marijuana use by heroin abusers as a factor in program retention. J Consult Clin Psychol 45:709-710). Among opioid-dependent individuals undergoing naltrexone therapy, intermittent cannabis users (with 1-80% of UDS positive for cannabis) fared better than cannabis abstinent or consistent cannabis users in terms of treatment retention and medication compliance (Raby et al., Intermittent marijuana use is associated with improved retention in naltrexone treatment for opiate-dependence (2009) Am J Addict 18:301-308.)

CB1 receptors influence the rewarding effects of opiates. CB1 receptor anatagonists block the development of morphine-induced conditioned place preference in rats and mice (Chaperon et al., Involvement of central cannabinoid (CB1) receptors in the establishment of place conditioning in rats (1998). Psychopharmacology (Berl) 135(4), 324-332.), and mice lacking CB1 receptors display reduced morphine-induced CPP (Rice et al., Conditioned place preference to morphine in cannabinoid CB1 receptor knockout mice (2002). Brain Res 945(1), 135-138.) CB1 receptor knockout mice do not acquire heroin self-administration. SR141716A dose-dependently reduces heroin self-administration in rats (Navarro et al., Functional interaction between opioid and cannabinoid receptors in drug self-administration (2001, J Neurosci 21(14), 5344-5350).

Thus CB1 antagonists, such as those provided in the present invention, can be used to selectively treat conditioned place preference and prevent the genesis of opioid dependency (Manzanedo et al., Cannabinoid agonist-induced sensitisation to morphine place preference in mice (2004).

While medical cannabis is used widely in conjunction with opioids, as well as in conjunction with the administration of opiate-based narcotics for the treatment of chronic and acute pain, there is a need for a more nuanced dosage administration that will precisely administer the cannabinoids that will alleviate dependency, rather than cultivate it.

Stimulant Addiction

Recent evidence also supports the involvement of the endocannabinoid system in the neurobiological processes related to stimulant addiction. Addiction to psychostimulants such as cocaine, amphetamine, and its derivatives (i.e., methamphetamine, N-methyl-3,4-methylenedioxymethamphetamine (MDMA)) is a significant public health problem affecting many aspects of social and economic life, with between 16 and 51 millions substance users worldwide (Oliere et al., Modulation of the endocannabinoid system: vulnerability factor and new treatment target for stimulant addiction (2013) Front Psychiatry 23; 4:109).

In recent decades, development of new treatments for psychostimulant addiction has been a major focus of multidisciplinary research efforts, and has included molecular approaches, preclinical behavioural studies, and clinical trials.

Soria and colleagues observed that CB1 receptor deletion impairs the acquisition of cocaine self-administration by mice, and both genetic and pharmacological CB1 receptor blockade reduces the motivation for cocaine under a progressive ratio schedule of reinforcement (Soria et al., Lack of CB1 cannabinoid receptor impairs cocaine self-administration (2005) Neuropsychopharmacology 30:1670-1680).

The CB1 receptor antagonist AM251 significantly attenuates the motivation for cocaine self-administration under a progressive ratio schedule of reinforcement (Xi et al., Cannabinoid CB1 receptor antagonists attenuate cocaine's rewarding effects: experiments with self-administration and brain-stimulation reward in rats (2008) Neuropsychopharmacology 33(7), 1735-1745), reduces methamphetamine self-administration (Vinklerova et al., Inhibition of methamphetamine self-administration in rats by cannabinoid receptor antagonist AM 251 (2002). J Psychopharmacol 16:139-143) and attenuates cocaine-induced enhancement in the sensitivity to brain stimulation reward (Xi et al., Cannabinoid CB1 receptor antagonists attenuate cocaine's rewarding effects: experiments with self-administration and brain-stimulation reward in rats (2008, Neuropsychopharmacology 33(7), 1735-1745).

Orio and colleagues found that the CB1 receptor influence on cocaine reward is enhanced by long periods of cocaine self-administration that result in progressive increases in cocaine intake (Orio et al., A role for the endocannabinoid system in the increased motivation for cocaine in extended-access conditions (2009) J Neurosci 29(15), 4846-4857). These observations show that neuroadaptations induced by extended cocaine exposure may recruit a CB1 receptor involvement in a progressive escalation of drug intake that results from extended periods of cocaine use.

Thus the targeted administration of selective CB1 receptor antagonists, according to the present invention, are useful in the alleviation of chemical dependency associated with, and withdrawal from, psychostimulants.

Alcohol Addiction

Alcohol is possibly the habit-forming drug that has recently been more studied for its relationships with the endocannabinoid signaling system (Hungund and Basavaraj appa, Are anandamide and cannabinoid receptors involved in ethanol tolerance? A review of the evidence (2000) Alcohol., 35:126-133.) This can be concluded from genetic studies that have proved a greater frequency for the appearance of a genetic polymorphism for the cannabinoid CB1 receptor in several subpopulations of alcoholic patients, in particular in alcoholics with severe withdrawal signs, such as delirium or seizures (Schmidt et al., Association of a CB1 cannabinoid receptor gene (CNR1) polymorphism with severe alcohol dependence (2002) Drug Alcohol Depend., 65, 221-224), or with antecedents of childhood attention deficit/hyperactivity (Ponce et al., Association between cannabinoid receptor gene (CNR1) and childhood attention deficit/hyperactivity disorder in Spanish male alcoholic patients (2003) Mol. Psychiatry, 8, 466-467), and also from biochemical studies that examined the effects of alcohol exposure on endocannabinoid signaling in laboratory animals or cultured nerve cells (Basavarajappa et al., Chronic ethanol administration down-regulates cannabinoid receptors in mouse brain synaptic plasma membrane (1998) Brain Res., 79, 212-218).

Chronic alcohol exposure modifies endocannabinoid levels in different brain regions, while pharmacological targeting of the endocannabinoid system has been reported to influence ethanol intake in laboratory animals. Pharmacological targeting of this system serves to reduce the incentive properties of alcohol, the signs of alcohol withdrawal, and/or the vulnerability to relapse. Mice treated with CB1 antagonists showed a significant reduction in self-administered alcohol consumption (Colombo et al., Suppressing effect of the cannabinoid CB1 receptor antagonist, SR 141716, on alcohol's motivational properties in alcohol-preferring rats (2004) Eur J Pharmacol 498: 119-123).

The instant invention provides for the administration of unique dosage forms of cannabinoids, including CB1 receptor antagonists like SR 141716 and other CBD antagonists, in the treatment of alcohol dependence.

Nicotine Addiction

CB1 knockout mice indicate a critical role of CB1 receptors in the rewarding effects of nicotine (Valjent et al., Behavioural and biochemical evidence for interactions between Delta 9-tetrahydrocannabinol and nicotine (2002) Br J Pharmacol 135(2), 564-578). Similarly, the administration of CB1 receptor antagonists like SR141716A have been successful in blocking the acquisition of nicotine-induced conditioned place preference in rats (Le Foll and Goldberg, Rimonabant, a CB1 antagonist, blocks nicotine-conditioned place preferences (2004) Neuroreport 15(13), 2139-2143; Forget et al., Cannabinoid CB1 receptors are involved in motivational effects of nicotine in rats (2005). Psychopharmacology (Berl) 181(4), 722-734); Cohen et al., SR141716, a central cannabinoid (CB1) receptor antagonist, blocks the motivational and dopamine-releasing effects of nicotine in rats (2002) Behav Pharmacol 13: 451-463).

Cannabinoid CB1 receptors are involved in motivational effects of nicotine in rats (2005) Psychopharmacology (Berl) 181(4), 722-734). Along with the more selective CB1 antagonist AM251, SR14176A dose-dependently reduces nicotine self-administration by rats (Cohen et al., SR141716, a central cannabinoid (CB(1)) receptor antagonist, blocks the motivational and dopamine-releasing effects of nicotine in rats (2002) Behav Pharmacol 13: 451-463).

The instant invention provides a measured dosage form capable of predictably administering precise, therapeutically effective amounts of cannabinoids, including, but not limited to, CB1 receptor antagonists as a means of reducing nicotine dependency.

Treatment of Adverse Effects Associated with Dependency and Withdrawal

High CBD intake relative to THC has been associated with lower scores on the positive dimensions of the CAPE (Community Assessment of Psychic Experiences) Scale, inhibition of psychotic symptoms, and reduced deficiencies in episodic memory (Englund et al., Cannabidiol inhibits THC-elicited paranoid symptoms and hippocampal-dependent memory impairment. J Pharmacol (2013) 27(1): 19-27). The present formulations present the advantage of an intentional dosage of synthetic or natural preparations with ideal pharmacology, to the exclusion of other cannabinoids, if desired, and their respective pharmacokinetic and pharmacodynamics influences. The "protective effects" afforded by extended or sustained release formulations can be harnessed by virtue of the present invention, along with the desired therapeutic effects of cannabidiols, either alone or in concert with therapeutically effective amounts of other cannabinoids.

The endocannabinoid system is intricately involved in the pathophysiology of depression, with CB1 receptors widely distributed in brain areas related to affective disorders, where expression is otherwise regulated by anti-depressants (Devane et al., Determination and characterization of a cannabinoid receptor in rat brain, Mol Pharmacol (1988) 34: 605-613; Hill and Gorzalka, Is there a role for the endocannabinoid system in the etiology and treatment of melancholic depression?Behav Pharmacol (2005) 16: 333-352; Hill et al., Regional alterations in the endocannabinoid system in an animal model of depression: effects of concurrent antidepressant treatment, J Neurochem (2008) 106: 2322-36).

Administration of CBD achieves characteristic effects of induced anti-psychotic and anxiolytic activity in subjects, and also attenuates the development of stress-induced behavioural consequences (Guimaraes et al., Antianxiety effect of cannabidiol in the elevated plus-maze. Psychopharmacology (1990) 100: 558-559; Resstel et al., Effects of cannabidiol and diazepam on behavioural and cardiovascular responses induced by contextual conditioned fear in rats. *Behav Brain Res* (2006) 172(2): 294-98; Resstel et al., 5-HT1A receptors are involved in the cannabidiol-induced attenuation of behavioural and cardiovascular-induced attenuation of behavioural and cardiovascular responses to acute restraint stress in rats. Br J Pharmacol (2009) 156(1): 181-88; Zuardi et al., Action of cannabidiol on the anxiety and other effects produced by delta 9-THC in normal subjects. Psychopharmacology (1982) 76: 245-50).

The instant invention is important and useful because CBD has a favorable profile in a model predictive of antidepressant-like activity in comparison to antidepressants, but such effects are only attainable at precise dosages, with smaller or higher doses producing no effect (Porsolt et al., Depression: a new animal model sensitive to antidepressant treatment. Nature (1977) 266:730-32; Zanelati et al., Antidepressant-like effects of cannabidiol in mice: possible involvement of 5-HT1A receptors. Br J Pharmacol (2010) 159:122-28). The present invention provides formulations which are capable of administering dosages in accordance with the most clinically appropriate pharmacokinetic and pharmacodynamic profile in order to achieve desired therapeutic effects in a patient presenting with a specific pathophysiology, such as major depressive disorder.

Sleep disturbances are a common adverse effect associated with withdrawal from chemical dependency, and for which certain cannabinoids can provide relief. The chemistry of CBD has been examined, and its central nervous system (CNS) pharmacological properties, including its anticonvulsant, anxiolytic, and sedative effects, have been documented (Chesher et al., (1975) Interaction of $D^9$-tetrahydrocannabinol and cannabidiol with phenobarbitone in protecting mice from electrically induced convulsions. J. Pharm. Pharmacol. 27:608-609; Pickens, (1981). Sedative activity of *Cannabis* in relation to its delta'-trans-tetrahydrocannabinol and cannabidiol content. Br. J. Pharmacol. 72:649-656; Russo and Guy, (2006) A tale of two cannabinoids: the therapeutic rationale for combining tetrahydrocannabinol and cannabidiol. Med. Hypotheses 66:234-246).

It has been shown that CBD improves sleep in individuals suffering from insomnia (Carlini and Cunha, Hypnotic and antiepileptic effects of cannabidiol. J. Clin. Pharmacol. 21 (suppl 8-9), 417S-427S). It has been successfully employed to block anxiety-induced REM sleep alteration via its anxiolytic effects (Hsiao et al., Effect of cannabidiol on sleep disruption induced by the repeated combination tests consisting of open field and elevated plus-maze in rats. Neuropharmacol (2012) 62: 373-84). Other studies have exhibited clinically significant improvements in sleep in subjects suffering from post-traumatic stress-related insomnia, even when subjects received no pharmaceutical medications to treat sleep disorders aside from cannabidiol oil (Shannon, Effectiveness of cannabidiol oil for pediatric anxiety and insomnia as part of posttraumatic stress disorder: a case report. Perm J (2016) 20(4): 16-005). The systemic acute administration of CBD increases total sleep time in subjects, in addition to increasing sleep latency in the light period of the day of administration (Chagas et al., Effects of acute systemic administration of cannabidiol on sleep-wake cycle in rats. J. Psychopharmacol (2013) 27:312-16).

Treatment of Drug-Seeking (Relapse)

Both positive and negative memories and conditioned cues associated with drug use perpetuate drug-seeking behaviour and the continued cycle of abuse.

Drug exposure produces powerful interoceptive effects that become associated with environmental cues, such that these cues alone can induce craving and promote relapse following periods of abstinence (Carter and Tiffany, Cue-reactivity and the future of addiction research (1999) Addiction 94: 349-51). In addition to conditioned drug memories, acute exposure to a preferred drug or pharmacologically related agent (that is, drug priming) and stressful events can precipitate relapse (Koob and Kreek, Stress, dysregulation of drug reward pathways, and the transition to drug dependence (2007) Am J Psychiatry 164: 1149-1159).

Animal models of relapse demonstrate an important cannabinoid influence on the reinstatement of extinguished drug-seeking and drug-taking behaviours. Cannabinoid $CB_1$ receptors control conditioned drug seeking. *Trends Pharmacol. Sci.* 26, 420-426. CB1R blockade attenuates relapse-like behaviour in rats, thus paving the way for numerous studies demonstrating a potent influence of CB1R signalling on relapse-like behaviour induced both by drug exposure and by drug-paired conditioned cues across multiple classes of abused drugs (Fattore et al., An endocannabinoid mechanism in relapse to drug seeking: a review of animal studies and clinical perspectives (2007). *Brain Res. Rev.* 53, 1-16.)

CB1R antagonism attenuates drug-primed, cue-induced and some forms of stress-induced reinstatement of cocaine- and methamphetamine-seeking behaviour in rats (Serrano and Parsons, (2011). Endocannabinoid influence in drug reinforcement, dependence and addiction-related behaviors. *Pharmacol. Ther.* 132, 215-241.)

Thus, CB1R signalling modulates drug-seeking for various pharmacologically distinct drugs. There is also evidence that CB1R antagonism blocks both cue- and priming-induced reinstatement of seeking behaviour for non-drug rewards, such as sucrose and corn oil (De Vries et al., (2005), Suppression of conditioned nicotine and sucrose seeking by the cannabinoid-1 receptor antagonist SR141716A. *Behav. Brain Res.* 161, 164-168.

Cannabinoid Pharmacokinetics

Dronabinol has been approved by the Food and Drug Administration for the control of nausea and vomiting associated with chemotherapy, as well as for appetite stimulation in patients suffering from wasting syndrome. While synthetic dronabinol is a recognized pharmaceutically active ingredient, natural botanic sources of THC are also known in the art. Any or all of these cannabinoids may be used in the present invention.

Marinol® is manufactured as a gelatin capsule containing dronabinol in a suspension of sesame oil. It is taken orally, and is available in round, soft gelatin capsules containing either 2.5 mg, 5 mg, or 10 mg dosages of dronabinol. It is presently prescribed for the treatment of cachexia in patients with AIDS, and for the treatment of nausea and vomiting associated with chemotherapy in cancer patients who have failed to respond to conventional antiemetic treatments. Like other oils provided in gelatin dosage forms, there is an urgent need for solid (powder and tablet) unique and con-trolled-release dosage forms of this drug, as provided in the instant invention.

Despite FDA approval, it is almost universally accepted that medical marijuana possesses many benefits over the synthesized dronabinol found in Marinol, and that, by prohibiting the possession and use of natural *Cannabis* and its myriad cannabinoids, patients are unnecessarily restricted to use of a synthetic substitute lacking the robust therapeutic efficacy of its natural analog. Anecdotal reports indicate that patients prescribed Marinol® report adverse psychoactive effects with greater frequency, lasting 4-6 hours, as well as drowsiness, dizziness, confusion, anxiety, impairment, and depression (Why Marinol® is not as good as marijuana, supra).

*Cannabis sativa*, in its crude form, often also possesses cannabinoids with undesirable effects in subjects, such as prolonged psychoactive effects. The present invention seeks to manipulate those properties and the pharmacokinetic profiles of the various cannabinoids within a novel drug delivery system in order to yield desired therapeutic effects in subjects over specific periods of time, while minimizing adverse effects.

Sativex® is another cannabinoid-based drug that is an improvement over Marinol® in certain aspects. It is an oral *Cannabis* spray consisting of natural cannabinoid extracts. It possesses greater bioavailability and uptake upon interaction with the subject's endocannabinoid receptors, and has a consequently reduced time for onset of action relative to that of the synthetic dronabinol in Marinol®.

In this aspect, it is a superior cannabinoid drug to Marinol®—but oral sprays are plagued by their own shortcomings, including long tmax values ranging from 1 to 4 h for Marinol® and 3.3 to 4.0 h for Sativex® (Davis M P. Oral nabilone capsules in the treatment of chemotherapy-induced nausea and vomiting and pain. *Expert Opin Investig Drugs*. (2008) 17:85-95; Karschner E L, Darwin W D, Goodwin R S, Wright S, Huestis M A. Plasma cannabinoid pharmacokinetics following controlled oral {Delta}9-Tetrahydrocannabinol and oromucosal *Cannabis* extract administration. *Clin Chem.* (2011) 57:66-75). Long times to reach maximal concentration can present a disadvantage for on-demand symptomatic treatment.

The alternative of existing gelatin-capsule formulations of Marinol® present their own challenges, as their variable pharmacokinetics result in significant variations in peak plasma concentrations (150-200%) (Naef M, Curatolo M, Petersen-Felix S, Arendt-Nielsen L, Zbinden A, Brenneisen R. The analgesic effect of oral delta-9-tetrahydrocannabinol (THC), morphine, and a THC-morphine combination in healthy subjects under experimental pain conditions. Pain. (2003) 105:79-88; Wall M E, Perez-Reyes M. The metabolism of delta 9-tetrahydrocannabinol and related cannabinoids in man. J Clin Pharmacol. (1981) 21:178S-89S; see also *Why Marinol® is Not as Good as Real Marijuana*, posted by Johnny Green on Mar. 5, 2012, www.theweedblog.com/why-marinol-is-not-as-good-as-real-marijuana, incorporated in its entirety accessed Mar. 5, 2017). This is unfavourable for accurate dose regulation. As a result of these shortcomings, Sativex® and Marinol® have not been widely adopted as a replacement for medical marijuana.

Further, Marinol® lacks several of the therapeutic benefits of other cannabinoids present in *Cannabis sativa*, of which there are more than 66. Synthetic dronabinol, the active ingredient in Marinol®, is itself a derivative or analog of one such compound (delta-9-tetrahydrocannabinol or THC). But importantly, several other cannabinoids in *Cannabis sativa*, in addition to naturally occurring terpenoids (oils) and flavonoids (phenols), have been clinically demonstrated to possess therapeutic utility. The presence of these myriad other therapeutically effective cannabinoids factors largely into patients' persistent preference for natural *Cannabis*.

One such cannabinoid is CBD, which, as set out above, has clinically demonstrated anxiolytic, analgesic, anti-psychotic, anti-epileptic, anti-spasmodic, and anti-rheumatoid arthritic properties. Natural CBD extracts, when administered in conjunction with natural or synthetic THC, are also capable of inhibiting undesirable effects of THC, such as its induction of anxiogenic, psychotic, and psychoactive activity in patients. Along with these inhibitory effects, CBD, administered with THC, has resulted in clinically significant reductions in pain, spasticity, and other symptoms in multiple sclerosis (MS) patients non-responsive to existing treatment options; this is particularly the case with severe or advanced-stage MS.

CBD has been shown to be neuroprotective against glutamate neurotoxicity (i.e., stroke); cerebral infarction (localized cell death in the brain); and ethanol-induced neurotoxicity, with CBD exhibiting greater protective properties than either ascorbate (vitamin C) or alpha-tocopherol (vitamin E). Clinical trials have shown CBD to possess anti-tumoral properties, inhibiting the growth of glioma (brain tumor) cells in a dose-dependent manner, and selectively inducing apoptosis (programmed cell death) in malignant cells, a significant clinical advantage. Dosage formulations of CBD and other cannabinoids can also be formulated into solid dosage forms according to the present invention.

Additional cannabinoids possessing clinically demonstrated therapeutic properties include: cannabinol (anti-convulsant and anti-inflammatory activity); cannabichromene (anti-inflammatory and anti-depressant activity); and cannabigerol (anti-tumoral and analgesic activity). The essential oil components (terpenoids) of *Cannabis sativa* exhibit anti-inflammatory properties, and its flavonoids express antioxidant activity.

Emerging clinical evidence suggests that cannabinoids may act to slow disease progression in certain autoimmune and neurologic diseases, including MS, amyotrophic lateral sclerosis (Lou Gehrig's disease), and Huntington's disease. (Johnny Green, supra). Dosage formulations of these cannabinoids can be formulated into solid dosage forms in accordance with the present invention.

Oral ingestion of Marinol® sidesteps the potential side effects of smoking, but because of the poor bioavailability of its constituent dronabinol, only 5-20% of orally-administered THC reaches the blood stream, and the drug may not attain peak effect until more than 4 hours after administration. (National Academy of Sciences, Institute of Medicine. Marijuana and Medicine: Assessing the Science Base. (1999) p. 203; Growing L., et al. Therapeutic use of *Cannabis*: clarifying the debate. Drug and Alcohol Review (1998)). Moreover, because dronabinol is metabolized slowly, its therapeutic and psychoactive effects may be unpredictable and vary considerably, both from one person to another, and in the same person, from one episode of use to another (Calhoun S., et al. Abuse potential of dronabinol. Journal of Psychoactive Drugs (1998) 30: 187-196; Morgan J., Zimmer L. Marijuana myths, marijuana facts: A review of the scientific evidence. P. 19). Thus, there is a need for improved bioavailability dosage forms of both natural and synthetic cannabinoids with more precise pharmacokinetics.

As a result of Marinol's® slow onset and poor bioavailability, scientists are developing a new formulation of pulmonary dronabinol, delivered with a pressurized metered dose inhaler (Medical News Today. New synthetic delta-9-THC inhaler offers safe, rapid delivery, phase I study. Apr. 17, 2005). Unlike oral synthetic THC, it's possible that pulmonary Marinol® (and by inference, its active ingredient, dronabinol) "could offer an alternative for patients when a fast onset of action is desirable", a significant improvement over onset times ranging from 1-4 h.

U.S. Pat. No. 6,403,126 (incorporated herein by reference in its entirety) discloses methods of extracting and purifying cannabinoids from *Cannabis* using organic solvent.

An analog of dronabinol, nabilone, is also available commercially.

US 20120231083 discloses a sustained release medicament, which results in delivery of a therapeutic level of one or more cannabinoids during a clinically relevant therapeutic window. The therapeutic window is a longer window than provided by an fast or even immediate release medicament such as Marinol®, containing an equivalent amount of the cannabinoid.

In contrast, oral administration of the present compositions provide therapeutic dosing while maintaining safe, side effect-sparing levels of cannabinoid. They also provide methods of precisely modulating the administration of the cannabinoids, and thereby treating patients with cannabinoid-sensitive disorders.

US 20060257463 discloses a method of transmucosally delivering a cannabinoid to a subject in need of treatment, comprising the steps of: administering to the subject a transmucosal preparation containing the cannabinoid wherein said transmucosal preparation is made by incorporating an effective amount of the cannabinoid via hot-melt extrusion technology, hot-melt molding, admixing, or a solvent cast technique into a film matrix or a reservoir containing the cannabinoid, and attaching said transmucosal preparation to the mucosa of the subject.

Pharmaceutical compositions comprising the cannabinoid active pharmaceutical ingredient, crystalline trans-($\pm$)-delta9-tetrahydrocannabinol, and formulations thereof, are disclosed in WO 2006133941. The invention also relates to methods for treating or preventing a condition, such as pain, comprising the administration to a patient in need thereof an effective amount of crystalline trans-($\pm$)-delta9-tetrahydrocannabinol. In specific embodiments, the crystalline trans-($\pm$)-delta9-tetrahydrocannabinol can be administered according to the methods for treating or preventing a condition such as pain, and can have a purity of at least about 98% based on the total weight of the cannabinoids.

US 2003/0229027 discloses oral cannabinoid formulations involving encapsulating the cannabinoids with sugar and sugar alcohols.

US 2005/0090468 discloses complexes of cannabinoids with methylated cyclodextrins.

US 2007/0104741 discloses a self-emulsifying drug delivery system alleged to improve dissolution, stability, and bioavailability of drug compounds of dronabinol or other cannabinoids.

US 20140100269 discloses oral cannabinoid formulations, including an aqueous-based oral donabinol solution, that are alleged to be stable at room or refrigerated temperatures.

U.S. Pat. No. 8,632,825 discloses the use of a combination of cannabinoids, particularly tetrahydrocannabinol (THC) and cannabidiol (CBD), in the manufacture of a medicament for use in the treatment of cancer.

U.S. Pat. No. 6,630,507 discloses that cannabinoids have antioxidant properties. This property makes them useful in the treatment and prophylaxis of a wide variety of oxidation-associated diseases, such as ischemic, age-related, inflammatory, and autoimmune diseases. The cannabinoids are found to have particular application as neuroprotectants, for example, in limiting neurological damage following ischemic insults, such as stroke and trauma, or in the treatment of neurodegenerative diseases, such as Alzheimer's disease, Parkinson's disease, and HIV dementia. Non-psychoactive cannabinoids, such as cannabidiol, are particularly advantageous to use because they avoid toxicity that is encountered with psychoactive cannabinoids at high doses, useful in the present invention.

U.S. Pat. No. 8,808,734 discloses liposomal and micelle formulations of cannabinoid analogues. U.S. 67/475,058 discloses composition for inhalation therapy comprising delta-9-tetrahydrocannabinol and semi-aqueous solvents.

Dosage and Administration of Dronabinol from FDA Document NDA 18-651/S-021; 500012 Rev September 2004:

Appetite Stimulation: Initially, 2.5 mg dronabinol capsules should be administered orally twice daily (b.i.d.), before lunch and supper. For patients unable to tolerate this 5 mg/day dosage, the dosage can be reduced to 2.5 mg/day, administered as a single dose in the evening or bedtime. If clinically indicated and in the absence of significant adverse effects, the dosage may be gradually increased to a maximum of 20 mg/day, administered in divided oral doses. Caution should be exercised in escalating the dosage because of the increased frequency of dose-related adverse experiences at higher dosages.

Antiemetic: Best administered at an initial dose of 5 mg/m2, given 1 to 3 hours prior to the administration of chemotherapy, then every 2 to 4 hours after chemotherapy is given, for a total of 4 to 6 doses/day. Should the 5 mg/m2 dose prove to be ineffective, and in the absence of significant side effects, the dose may be escalated by 2.5 mg/m2 increments to a maximum of 15 mg/m2 dose. Caution should be exercised in dose escalation, however, as the incidence of disturbing symptoms increases significantly at maximum dose.

Despite all of the work on new dosage formulations of cannabinoids and dronabinol, there is a need in the art for simple, inexpensive, improved dosage forms that have an improved profile with faster onset, extended release profiles, and lower inter-subject variability than currently available cannabinoid products.

In the 1970s and 1980s, there were almost no marketed drugs with less than 10 µg/ml solubility (10-100 µg/ml was considered low) (Solid Dispersions: New Approaches and Technologies in Drug Delivery, Controlled Release Society; Rutgers, N.J., 2 Jun. 2009, Craig A. McKelvey, Merck & Co., Inc., hereinafter "McKelvey"). Presently, it is estimated that more than 60% of active pharmaceutical ingredients (APIs) in development have poor bioavailability due to low aqueous solubility (WO 2013040187, citing Manufacturing Chemist, March 2010, 24-25). At least partially as a result of advances in combinatorial chemistry and molecular screening methods for identifying potential drug candidates, an increasing number of insoluble drugs are being identified. Formulation methods are also evolving in an attempt to keep up but formulation and expense are often problematic.

Poor solubility of compounds may result in ineffective absorption, which is an important part of the high clinical failure rate due to poor pharmacokinetics. Drugs with very low aqueous solubility often have sizeable within- and between-subject pharmacokinetic variability, making study design and the conduct of clinical studies very challenging, the assessment of dose-response and exposure-response relationships difficult, and resulting in difficult dose determination. Water insoluble drugs often have high propensity for drug interactions at the absorption level, such as food interactions, and interactions with gastrointestinal "GI" prokinetic agents, especially if these drugs also have narrow therapeutic windows. There is an on-going need in the art for better formulation technologies for poorly soluble drugs (Jain et al., Asian J Pharm Clin Res, Vol 5, Suppl 4, 2012, 15-19).

A drug substance is generally considered highly soluble when the highest dose strength is soluble in 250 ml water over a pH range of 1 to 7.5. A drug is generally considered highly permeable when the extent of absorption in humans is determined to be 90% of an administered dose, based on the mass balance or in comparison to an intravenous dose (drug and metabolite). A drug product is generally considered to dissolve rapidly when 85% of the labeled amount of substance dissolves within 30 minutes, using USP apparatus I or II in a volume of 900 ml buffer solution. (Gothoskar A. V. Biopharmaceutical classification of drugs. Pharm Rev. 2005; 3:1.).

For BCS Class II drugs that have low bioavailability resulting from poor solubility and the inability to dissolve rapidly the selection of formulation is often a major hurdle preventing the development of a successful oral drug product. Certain technologies have recently been developed to aid in the formulation of these drugs including: salt formation, size reduction, co-solvency, pH manipulation, surfactant and micelle use, inclusion complexes, lipid formulations, and solid dispersions. Jain et al. Asian J Pharm Clin Res, Vol 5, Suppl 4, 2012, 15-19).

According to the "Intra-Agency Agreement Between the Eunice Kennedy Shriver National Institute of Child Health and Human Development (NICHD) and the U.S. Food and Drug Administration (FDA) Oral Formulations Platform-Report 1" dronabinol is a class 2 or class 4 drug with low solubility and unknown permeability. Thus it may be formulated in the same manner as a class 2 drug.

Absorption and distribution: Dronabinol capsules are almost completely absorbed (90 to 95%) after single oral doses. Due at least in part to the effects of first pass hepatic metabolism only 10 to 20% of the administered dose reaches the systemic circulation (FDA document NDA 18-651/S-021).

The advantages of controlled release products are well known in the pharmaceutical field. Controlled release drug formulations may be useful to reduce the frequency of drug administration (especially in the case of drugs with short compound half lives), improve patient adherence, reduce drug toxicity (local or systemic associated with high peak exposure), reduce drug level fluctuation in blood, stabilize medical condition with more uniform drug levels, reduce drug accumulation with chronic therapy, improve bioavailability of some drugs because of spatial control, and reduce total drug usage when compared with fast or even immediate release drugs.

Oral controlled release delivery systems should ideally be adaptable so that release rates and profiles can be matched to physiological and temporal requirements.

Mechanical devices aside, interaction between a drug and a polymeric material often forms the basis of controlled oral drug delivery. A polymer at certain concentrations in a solution imposes pathways for drug diffusion. Polymers that dissolve in or otherwise hydrate in aqueous media can alter the drug diffusion process in a time-dependent manner. For example, a commonly used material, hydroxypropyl methylcellulose (HPMC), which is water soluble, behaves as a swellable absorptive polymer in the limited volumes of aqueous media in the gastrointestinal tract. Drug dispersed in this polymer, as in monolithic tablets, diffuses through the viscous hydrated polymer at a rate dependent on the movement kinetics of the polymer chains. The faster these relax, the faster the diffusion rate.

Development of dosage form depends on chemical nature of the drug and polymers, the matrix structure, swelling, diffusion, erosion, the release mechanism and the in vivo environment.

Hydrophilic polymers like HPMC may also control drug release by erosion mechanisms. After consumption of the dosage form, the GI tract fluid encounters the dosage unit, causing the polymer to hydrate and swell. Weakened mechanical properties in the swollen state may cause the hydrated polymer to break away from the prime particle (compact or pellet). Drug release may therefore be controlled by a combination of diffusion and erosion. Such release mechanisms can apply to systems where drug is dispersed in or coated with polymer.

Extended release dosage forms of class 2 drugs often require expensive, difficult, and proprietary osmotic delivery systems such as Alza's Oros™ and Duros™ technologies. (See U.S. Pat. Nos. 4,612,008; 4,327,725; 4,765,989; and 4,783,337). Other technologies have been developed to exploit diffusion, erosion, and other physicochemical mechanisms and provide drug and disease-specific release profiles. Examples also include the release from a Contramid™ tablet controlled by the degree of crosslinking of high amylase starch.

Simple extended release formulations include the use of water insoluble polymers which can be used in coating-based extended drug release formulations. These include methacrylate- or acrylate-based polymers with low permeability.

Hydrophilic functional groups such as trimethylaminoethyl methacrylate can improve permeability and swellability in water, thus altering release behaviors.

Various drug candidates such as diltiazem hcl, carbamazepine, metoprolol, oxprenolol, nifedipine, glipizide have been formulated as osmotic delivery systems. Problems with such osmotic delivery systems include the need for special equipment for making an orifice in the system; residence time of the system in the body varies with the gastric motility and food intake; such systems may cause irritation or ulcer due to release of saturated solutions of drug. Online Available at www.thepharmajournal.com. THE PHARMA INNOVATION Vol. 1 No. 7 2012 "www.thepharmajournal.com" Page|116 Osmotic-Controlled Release Oral Delivery System: An Advanced Oral Delivery Form. Nitika Ahuja, Vikash Kumar, Permender Rathee. Accessed Mar. 5, 2017.

The instant invention solves many problems associated with current delivery of cannabinoids and provides for both cannabinoid immediate and sustained release dosage forms in a technically and economically efficient and surprising manner.

In general, the most desirable oral dosage form is a tablet, and it would be advantageous if a cannabinoid containing tablet could be made available which does not suffer from the obstacles of prohibitively expensive drug delivery systems, nor the need for smoking or "edible" dosage forms. None of the documents described above enable controlled release cannabinoid tablets that combine the requirements for instant relief with long lasting effects. There is a need for new cheap and stable dosage formulations, especially tablets, comprising multiple effective dose of cannabinoids or derivatives thereof. There is also a need for a stable cannabinoid powder.

Another aspect the invention provides a pharmaceutical or nutraceutical composition in the form of a tablet for oral administration comprising cannabinoid wherein said tablet is preferably formed from a pharmaceutically or even nutraceutically acceptable powder.

By "nutraceutical" is meant a composition that provides medical or health benefits, including the prevention and treatment of disease. Dietary supplements and natural health products are examples of nutraceuticals. In many places natural cannabinoids are considered nutraceuticals. Within the context of this invention it is understood that the term "drug" is used generically to include prescription and non-prescription pharmaceutical products as well as nutraceuticals including dietary supplements, natural health products, medicinal foods, drinks, candy bars with active ingredients and all other similar delivery methods whether approved or unapproved.

Viewed from another aspect the invention provides a pharmaceutical or nutraceutical tablet as hereinbefore described for use in the treatment or prophylaxis of all of the disorders that medical marijuana and drabinol is used for at the present time.

As used herein, the term "drug" includes not only FDA approved pharmaceuticals but also natural medicines, alternative medicines, and dietary supplements and generally refers to all forms of cannabinoids.

DETAILED DESCRIPTION OF THE INVENTION

Extending drug release ("sustained release") from a dosage form can prolong its action and attenuate peak plasma levels, thereby obviating concentration-related side effects. It can also optimize the efficacy of one or several of its constituent APIs by matching systemic presence with other time-related effects. As discussed above, sustained release drug forms can be achieved by embedding the drug in a matrix that prevents fast or even immediate release, and which delivers excipient at a desired rate consistent with absorption or disposition requirements. Such a formulation can also be coated with an "fast or even immediate release" layer, or as further described herein pressed into two or more layers of different actives and dosage forms all within one tablet. This allows a larger arsenal of pharmacokinetic pathways for administration, with varying time-release profiles, and thereby tailoring a drug to the desired effects in the end user. By employing a more precise drug delivery mechanism than a dosage form such as a simple oil emulsion, greater bioavailability is achieved while inter- and between-subject variability is minimized. With respect to cannabinoid-related medicaments specifically, greater precision and control can be achieved in the dosage of cannabinoids which exhibit greater adverse side effects, such as psychoactive or an anxiogenic activity in the end user, and/or modulated by a consistent or even zero-order release of cannabinoids known to inhibit those adverse effects by competitively binding to receptors in the endocannabinoid system (e.g., CBD).

A wide variety of materials can be used to design the most appropriate release profile and provide a viable and consistent mode of manufacture. The present invention solves this problem in a novel way.

As discussed above, BCS Class II drugs present challenges for oral delivery, let alone attempts at zero order pharmacokinetics. As used herein, zero order kinetics are drug release kinetics that are independent of the existing concentration or initial concentration of the active drug. In other words, the drug release is controlled by the dosage form rather than the active(s) concentration. In particular embodiments, the dosage form may provide a zero order release from mere seconds to about 12 hours after administration. In certain embodiments, the dosage form releases more than about 90% or more of the active agent in less than about 24 hrs. In particular embodiments, the dosage form may provide a zero order rate of release for at least a portion of the delivery period. In other embodiments, the dosage form may provide an ascending rate of release for at least a portion of the delivery period. In yet other embodiments, the dosage form may provide a fast initial rate of release followed by a slower rate of release of the remaining active agent(s).

The present invention also allows the differential release of different cannabinoids.

The modified release formulations of cannabinoids of the present invention represent a significant improvement over existing formulations and delivery methods of cannabinoids.

The present invention includes a novel granulation method for formulating cannabinoids and subsequently into bi-layer or even multi-layer tablets.

The benefits of the invention include maintaining cannabinoids in a soluble, hydrophilic state in contact with body fluids.

The present invention provides a deceptively simple but novel and elegant formulation solution to the problem of formulating modified release versions of cannabinoids involving a few simple ingredients combined in an extremely inventive and unique way.

Cannabinoid Extract Resin

The cannabinoid extracts of the present invention can be extracted and formulated to provide a number of sustained release combinations useful in the present invention. Of particular interest are 100 percent THC tablets, 100% CBD tablets, 10:1 THC/CBD, 1:10 THC/CBD, and 50:50 THC/CBD although other variations of sustained release granules and tablets are encompassed by the present invention and may be desirable in specific situations. [001] Certain formulations contain THC and CBD in defined ratios by weight. Preferred formulations may contain but are not limited to the following ratios by weight of THC and CBD:—greater than or equal to 19:1 THC:CBD, greater than or equal to 19:1 CBD:THC, 4.5:1 THC:CBD, 1:4 THC:CBD and 1:2.7 THC:CBD. Other ratios may be chosen depending on the particular application.

In a preferred embodiment the formulations may contain specific, pre-defined ratios by weight of different cannbinoids, e.g. specific ratios of CBD to THC, or tetrahydrocannabinovarin (THCV) to cannabidivarin (CBDV), or THCV to THC. Certain specific ratios of cannabinoids have been found to be clinically useful in the treatment or management of specific diseases or medical conditions.

The dosage form may also contain, in addition to the cannabinoid(s), a further active agent, which may be an opiate, for example morphine or dietary supplements as outlined herein.

The cannabinoids may be present as pure or isolated cannabinoids or in the form of plant extracts. Where a plant extract is used to obtain CBDs it is preferable that the THC content is less than 5% by weight of the total cannabinoids, more preferably less than 4% through 3%, 2% and 1%. THC can be selectively removed from extracts using techniques such as chromatography.

Preferred cannabinoids include, but are not limited to, tetrahydrocannabinoids, their precursors, alkyl (particularly propyl) analogues, cannabidiols, their precursors, alkyl (particularly propyl) analogues, and cannabinol. In a preferred embodiment the formulations may comprise any cannabinoids selected from tetrahydrocannabinol, A9-tetrahydrocannabinol (THC), A8-tetrahydrocannabinol, A9-tetrahydrocannabinol propyl analogue (THCV), cannabidiol (CBD), cannabidiol propyl analogue (CBDV), cannabinol (CBN), cannabichromene, cannabichromene propyl analogue and cannabigerol, or any combination of two or more of these cannabinoids.

It has particularly been observed by the present applicant that combinations of specific cannabinoids are more beneficial than any one of the individual cannabinoids alone. Preferred embodiments are those formulations in which the amount of CBD is in a greater amount by weight than the amount of THC.

One preferred daily dose of THCV is at least 1.5 mg, more preferably at least 5 mg through 10 mg to 15 mg or more.

In another aspect, the THCV may be used in combination with at least a second, therapeutically effective cannabinoid, preferably CBD.

The CBD may be present in an amount which will provide a daily dose of 200 mg, more preferably 600 mg and as much as 800 mg or even more.

One preferred daily dose of CBD is at least 25 mg, more preferably at least 5 mg through 10 mg to 15 mg or more.

In another aspect, the CBD maybe used in combination with at least a second, therapeutically effective cannabinoid, preferably AM4113, SR141716A, other novel CB1 receptor antagonists.

The CBD may be present in an amount which will provide a daily dose of 25 mg, more preferably 30 mg and as much as 50 mg or even more.

Preferred formulations may include natural extracts of *Cannabis*.

Bi-Layer or Multi-Layer Tablets

A drug formulation providing fast release of a constituent and a further release of constituent over a delayed or sustained period of time can be achieved by making a combination dosage unit. Particularly where certain drugs are known to competitively inhibit one another, it can be desirable to provide for co-administration in a time dependent manner.

In contrast to traditional cannabinoid-based drugs and their associated variability and adverse side effects, the present invention presents a more precise, nuanced approach to cannabinoid administration.

In certain embodiments, the present invention comprises a customized bilayer or even multi-layer tablet comprised of at least two layers including: a fast or even immediate release layer and a modified release layer. The modified release layer may comprise a cannabinoid (e.g, dronanibinol powder, cannabinoid resin) combined with 2-hydroxypropyl-β-cyclodextrin. In one aspect, the modified release layer is a delayed release layer.

In addition, delayed release can be achieved using an enteric formulation (e.g., a tablet coated with a gastric resistant polymer, for example, Eudragit L100-55. Other gastric resistant polymers include: methacrylates, cellulose acetate phthalate, polyvinyl acetate phthalate, hydroxypropyl methylcellulose phthalate, in particular, Aquateric, Sureteric, HPCMP-HP-55S.

The enteric coated tablet may be either of: a single layer tablet, where the active agents are admixed prior to compression into a tablet form, or a multi-layer tablet, such as a bi- or tri-layer tablet, wherein each active agent or combinations of active agents are present in a discrete layer within the compressed tablet form. The discrete tablet layers can be arranged as required to provide for modified, or non-modified, release of each agent.

In a further embodiment the modified release layer may be a sustained release layer. The present invention employs novel compositions as the sustained release formulation to present distinct advantages over the art. The sustained release tablets comprise a therapeutically effective amount of cannabinoid and sustained release excipients.

Multi-layer tablet dosage forms are capable of achieving unique product performance objectives not otherwise achievable by conventional tablets (Vaithiyalingam, S R, Sayeed, V A. (2010). Critical factors in manufacturing multi-layer table include assessing material attributes, process controls, manufacturing process and product performance. *Int. J. Pharm.*, 398: 9-13). Multi-layer tablets have several advantages, including control of the delivery rate of either single (Bogan, 2008) or two or more different active pharmaceutical ingredient(s) the separation of incompatible APIs from one another or controlled release of APIs from one layer through utilization of the functional property of the other layer (i.e., osmotic property) (Vaithiyalingam, S R, Sayeed, V A. (2010). Multi-layer tablet modifications may include variation of the total surface area available for the API layer, either by sandwiching with one or two inactive layers in order to achieve swellable/erodible barriers for modified release.

Bilayer tablets present manufacturing and design challenges, including the design of tablets that do not fracture at the interface because of insufficient adhesion (Akseli, I., et al. (2013). Mechanistic characterization of bilayer tablet formulations. *Powder Technol.* 236: 30-36; Kottala, N., et al. (2013). Characterization of interfacial strength of layered powder-compacted solids. *Powder Technol.* 239: 300-307), resulting in delamination during manu-facturing, packaging, and storage (Klinzing, G., Zavaliangos, A. (2013). Understanding the effect of environmental history on bilayer tablet interfacial shear strength. *Pharm. Res.* 30: 1300-1310; Kottala, N., et al. (2012). Influence of compaction properties and interfacial topography on the performance of bilayer tablets. *Int. J. Pharm.* 436: 171-178; Kottala, N., et al. (2012). Evaluation of the performance characteristics of bilayer tablets: Part I. Impact of material properties and process parameters on the strength of bilayer tablets. *AAPS Pharm Sci Tech* 13: 1236-1242; Kottala, N., et al. (2012). Evaluation of the performance characteristics of bilayer tablets: Part II. Impact of environmental conditions on the strength of bilayer tablets. *AAPS Pharm Sci Tech* 13: 1190-1196.), as well as other problems, such as binding, sticking, picking, filming, capping, and chipping (Fung K Y, Ng K M. (2009). Product-centered processing and manufacturing: pharmaceutical tablets and capsules. *AIChE. J.*, 49(5): 1193-1215.)

The design and development of solid dosage forms rely on the physicochemical and mechanical properties of the active, excipient components and mixtures thereof (Lyer R M, et al. (2014). The impact of roller compaction and tablet compression on physicomechanical properties of pharmaceutical excipients. *Pharm Dev Technol*, 19)5_: 583-592.) The physical properties are closely linked to final product specifications such as purity, uniformity, dissolution, stability, appearance and mechanical durability (Hlinak A J, Kuriyan K, Morris K R, et al. (2006). Understanding critical material properties for solid dosage form design. *J Pharm Innovation* September/October: 12-17.). While physical properties clearly influence powder flow and compression, the effects of mechanical properties of materials on their behaviour during processing has been demonstrated by instrumented tablet press, compaction simulator and mechanical testing devices (Vachon M G, Chulia D. (1999). The use of energy indices in estimating powder compaction functionality of mixtures in pharmaceutical tableting. *Int J Pharm* 177:183-200.).

In particular, studies have shown that tablet hardness, disintegration time and friability are markedly influenced by tablet hardness and compression force (Kathpalia, H., et al. (2014). Controlled release orally disintegrating tablets: A review. *IJPSR*, 24(1), 35-42.). The hardness, or "break force", of solid tablets serves as an important quality-control specification. An extremely hard tablet could indicate excessive bonding potential between active ingredients and excipients, which can lead to increased disintegration times and prevent proper dissolution of the tablet needed for an accurate dosage, whereas an excessively soft tablet may signify weak bonding and a likelihood of high friability and premature disintegration upon ingestion, as well as fracture, chipping, or breaking throughout the various stages of manufacture, such as coating and packaging. (Chiang E. (2013). Measuring tablet hardness: a primer. *Pharmaceutical Technology*, 37(6): 42.). Additionally, capping and lamination, or the horizontal and vertical breakup of the tablet, are caused by expansion of air entrapped in granulation which cannot escape during compression, and can be improved by reducing compression pressure (Fung K Y, Ng K M. (2009). Product-centered processing and manufacturing: pharmaceutical tablets and capsules. *AIChE. J.*, 49(5): 1193-1215). Reducing compression pressure can also assist in shortening disintegration time by increasing porosity, as well as in the prevention of capping and lamination (horizontal and vertical breakup of the tablet) caused by the expansion of air entrapped in granulation, which cannot escape during compression. For a weak tablet, bonding force among particles can be increased by increasing the compaction pressure.

The development and production of quality bilayer tablets requires a comprehensive understanding of the product and process in order to achieve accuracy in weight control of each individual layer, de-lamination/layer-separation during manufacturing and storage, and sufficient tablet breaking force and prevention of cross-contamination between the layers (Vaithiyalingam, S R, Sayeed, V A. (2010). The present invention may use two separate hardnesses to deliver two separate and distinct formulae in one unit dose, in which there is minimal contact between the two layers for improved release profile and product stability. Tablets are compressed using a double sided tablet press, in which the first tablet layer is partially created using one premix, without ejection from the die cavity, followed by a second filling using the other formulation, and final compression and ejection from the tablet press.

Hardness may be a critical parameter for the bilayer tablets of the invention. During the development stage, optimum tablet compression parameters are determined by the physical parameters of the tablet (i.e. hardness of $1^{st}$ layer, then total hardness of bilayer), which also affects the time release profile.

It is herein understood that the fast or even immediate release of a therapeutically effective amount of medicinal ingredients, e.g., cannabinoids, such as dronabinol, from the first layer will promote the onset of their therapeutic effects. Additionally, it is herein understood that a further release of cannabinoids, e.g. cannabidiol, from about 2 hours to about 7 hours, will act to maintain their therapeutic effects over a delayed or sustained period of time.

The dosage form of the formulation may be provided in accordance with customary processing techniques for drug formulations and/or supplements in any of the forms mentioned above. Additionally, the formulation set forth in the example embodiment herein may contain any appropriate number and type of excipients, as is well known in the art.

Sustained Release Layers

The primary purpose of drug delivery systems is to deliver the necessary amount of drug to the targeted site for a necessary period of time, both efficiently and precisely (Drug Delivery System; Juliano R L, Ed., Oxford University Press: New York, 1980; *Recent Advances in Drug Delivery Systems*; Anderson J M, Kim, S W, Eds., Plneum Press, New York, 1984; *Drug Targeting*, Buri P, Gumma A, Eds., Elsevier: Amsterdam, 1985). To design advanced dosage forms capable of carrying out this task with respect to BCS class II drugs in particular, suitable carrier materials are employed to overcome the undesirable properties of those drug molecules.

Cyclodextrins (sometimes called cycloamyloses) are a family of compounds made up of sugar molecules bound together in a ring (cyclic oligosaccharides).

Cyclodextrins are composed of 5 or more α-D-glucopyranoside units linked 1→4, as in amylose (a fragment of starch). The 5-membered macrocycle is not natural. Recently, the largest well-characterized cyclodextrin contains 32 1,4-anhydroglucopyranoside units, while as a poorly characterized mixture, at least 150-membered cyclic oligosaccharides are also known. Typical cyclodextrins contain a number of glucose monomers ranging from six to eight units in a ring, creating a cone shape:

α (alpha)-cyclodextrin: 6-membered sugar ring molecule
β (beta)-cyclodextrin: 7-membered sugar ring molecule
γ (gamma)-cyclodextrin: 8-membered sugar ring molecule α- and γ-cyclodextrin are being used in the food industry.

All of these cyclodextrins can be employed in the present invention.

Cyclodextrins are produced from starch by means of enzymatic conversion. Due to their ability to form host-guest or inclusion complexes with hydrophobic, biologically active agents, which is imparted by their unique structure ands hydrophobic cyclodextrin cavity, cyclodextrins are able to serve as enabling excipients for pharmaceutical, food, cosmetic, and other applications (Kurkov S V, Ukhatskaya E V. Drug/cyclodextrin: beyond inclusion complexation. J Incl Phenom Macrocycl Chem (2011) 69:297-301; Szente, L., & Szejtli, J. (2004). Cyclodextrins as food ingredients. Trends in Food Science & Technology, 15(3-4), 137-142], pharmaceutical, [Stella, V., & He, Q. (2008). Cyclodextrins. Toxicologic Pathology, 36(1), 30-42] drug delivery, [Laza-Knoerr, A. L., Gref, R., & Couvreur, P. (2010). Cyclodextrins for drug delivery. Journal of Drug Targeting, 18(9), 645-656.). As a result, these molecules have found a number of applications in a wide range of field.

Cyclodextrins Permit Improved Solubilization of Cannabinoids

Because cyclodextrins are hydrophobic inside and hydrophilic outside, they can form complexes with hydrophobic compounds. Thus they can enhance the solubility and bioavailability of such compounds. This is of high interest for pharmaceutical as well as dietary supplement applications in which hydrophobic compounds are to be delivered.

While crown ethers and calixarenes are also capable of forming host-guest complexes, only cyclodextrins have been approved for use in both pharmaceutical formulations and food products (Kurkov S V, supra). The most common pharmaceutical application of cyclodextrins is to enhance the solubility, stability, and bioavailability of drug molecules (*Cyclodextrins and their Industrial Uses*, Duchene, D., Ed.; Editions de Sante: Paris, 1987; Szjetli, J. *Cyclodextrin Technology*; Kluwer: Dordrecht, The Netherlands, 1988; Uekama, K. *YYakugaku Zasshi,* 1981, 101, 857; Sjetli, J., *J. Incl. Phenom.,* 1983, 1, 135).

Cyclodextrins can solubilize hydrophobic drugs in pharmaceutical applications, and crosslink to form polymers used for drug delivery. [Laza-Knoerr, A. L., Gref, R., & Couvreur, P. (2010). Cyclodextrins for drug delivery. Journal of Drug Targeting, 18(9), 645-656. One example is Sugammadex, a modified γ-cyclodextrin which reverses neuromuscular blockade by binding the drug rocuronium. Other than the above-mentioned pharmaceutical applications, cyclodextrins can be employed in environmental protection: these molecules can effectively immobilise inside their rings toxic compounds, like trichloroethane or heavy metals, or can form complexes with stable substances, like trichlorfon (an organophosphorus insecticide) or sewage sludge, enhancing their decomposition.

Typical cyclodextrins are constituted by 6-8 glucopyranoside units, can be topologically represented as toroids with the larger and the smaller openings of the toroid exposing to the solvent secondary and primary hydroxyl groups respectively. Because of this arrangement, the interior of the toroids is not hydrophobic, but considerably less hydrophilic than the aqueous environment and thus able to host other hydrophobic molecules. In contrast, the exterior is sufficiently hydrophilic to impart cyclodextrins (or their complexes) water solubility.

The formation of the inclusion compounds greatly modifies the physical and chemical properties of the guest molecule, mostly in terms of water solubility. This is one reason why cyclodextrins have attracted much interest in many fields, especially pharmaceutical applications: because inclusion compounds of cyclodextrins with hydrophobic molecules are able to penetrate body tissues, these can be used to release biologically active compounds under specific conditions. In most cases the mechanism of controlled degradation of such complexes is based on pH change of water solutions, leading to the loss of hydrogen or ionic bonds between the host and the guest molecules. Alternative means for the disruption of the complexes take advantage of heating or action of enzymes able to cleave α-1,4 linkages between glucose monomers.

α-Cyclodextrin has been authorized for use as a dietary fiber in the European Union since 2008. In 2013 the EU commission has verified a health claim for alpha-cyclodextrin. The EU assessment report confirms that consumption of alpha-cyclodextrin can reduce blood sugar peaks following a high-starch meal. Weight loss supplements are marketed from alpha-cyclodextrin which claim to bind to fat and be an alternative to other anti-obesity medications.

Due to its surface-active properties, α-cyclodextrin can also be used as emulsifying fiber, for example in mayonnaise as well as a whipping aid, for example in desserts and confectionary applications.

β-cyclodextrins are the main ingredient in P&G's product Febreze which claims that the β-cyclodextrins "trap" odor causing compounds, thereby reducing the odor.

The cavity of the 7-membered β-cyclodextrin and 8-membered γ-cyclodextrin offer enough space even for comparatively large molecules, and are able to form the most stable complexes (Uekama, K., et al. (1983). Improvement of dissolution and absorption characteristics of benzodiazepines bycyclodextrin complexation. *Int. J. Pharm.*, 10:1-15; Seo, H. et al. (1983) Enhancement of oral bioavailability of spironolactone by β- and γ-cyclodextrin complexations. *Chem. Pharm. Bull.*, 31:286-291; Otagiri, M. et al. (1983) Inclusion complex formations of the anti-inflammatory drug flurbiprofen with cyclodextrins in aqueous solution and in solid state, *Acta Pharm. Suec.* 20:11-20.].

Methylation or alkylation of β-cyclodextrin functions with different substituents have been used to solve the problems of the aggregation of cyclodextrins, and the interaction of surrounding water molecules, which otherwise results in low aqueous solubility and poor feasibility as natural drug carriers (Uekama K., Hirayama F., Irie T., Cyclodextrin Carrier Systems, Chem Rev. (1998) 98: 2045-76). Hydroxoalyklated cyclodextrins are amorphous structures of chemically related components with different degrees of substitution (Pitha, J., J. Pharm. Sci. (1985), 74, 987; Mueller, B. W.; U. Brauns, Int. J. Pharm. 1985, 26, 77; Yoshida, A.; Arima, H.; Uekama, K.; Pitha, J. Int. J. Pharm. 1988, 46, 217; Yoshida, A.; Yamamoto, M.; Irie, T.; Hirayama, F.; Uekama, K. Chem. Pharm. Bull. 1989, 37, 1059; Brewster, M. E.; Simpkins, J. W.; Hora, M. S.; Stern, W. C.; Bodor, N. J. Parenter. Sci. Technol. 1989, 43, 231). This multicomponent character prevents any crystallization, and thereby results in drastically increased aqueous solubility (>50%, w/v), while also preserving the complexing properties of the starting compound and allowing for solubilization (Uekama K., supra.; Muller B, Brauns U. Solubilization of drugs by modified β-cyclodextrins. Intl J Pharm 1985; 26: 77-88.] In addition, studies have shown a stabilizing effect on aqueous solutions, in which decomposition was delayed.

As mentioned above, the formation of inclusion compounds or "inclusion complexes", in which each guest molecule is surrounded by the hydrophobic environment of the cyclodextrin cavity (Uekama K., supra.), modifies the physical, chemical, and biological properties of the guest molecule, mostly in terms of water solubility, and allows hydrophobic molecules to penetrate body tissues and release biologically active compounds. Studies conducted on the use of indomethacin as a guest molecule, which normally undergoes controlled degradation by hydrolytic cleavage with a rate constant depending on the pH of the solution [Krasowska, H. (1974) Kinetics of indomethacin hydrolysis. Acta. Pharm. Jugoslav. 24:13-200.], was found to undergo delayed decomposition when it was solubilized by hydroxyethyl-β-cyclodextrin. Both of the above factors have important implications for the absorption of the cannabinoids according to the present invention.

Cyclodextrins Permit Improved Stabilization of Cannabinoids (Decreased Variability in Dosage)

Present shortcomings in available cannabinoid medications pertain to the large inter- and between-subject variability resulting from the gelatin capsules and oil suspensions currently on the market, including Marinol® and Sativex®, as set out above. Available cannabinoid medicaments do not attain peak plasma concentrations for between 1 and 4 h, and due to slow metabolism, their therapeutic effects vary considerably from person to person and use to use. There is a need for improved dosage forms of both natural and synthetic cannabinoids with more precise pharmacokinetics.

The present invention overcomes those shortcomings partially through the use of cyclodextrins in a sustained release layer and via the precision they are capable of achieving with respect to the pharmacokinetics of their guest drug molecules.

Cyclodextrins are known to accelerate or decelerate various kinds of reactions, exhibiting many kinetic features shown by enzyme reactions, i.e. catalyst-substrate complex formation, competitive inhibition, saturation, and stereospecific catalysis (Bender M L, Komiyama M. Cyclodextrin Chemistry; Springer-Verlag: Berlin, 1978). When an ester group of guest molecules is fixed in close proximity to the catalytic site of cyclodextrins, i.e., secondary hydroxyl groups, it experiences an acceleration in hydrolysis. On the other hand, hydrolysis is decelerated when the ester group is included deeply inside the cavity (Uekama K., supra.)

The rate of reactions such as decarboxylations and trans-cis isomerizations is changed by the inclusion because the guest is transferred from a polar environment of water to a less polar one of cyclodextrin cavity (i.e., microsolvent effect) (Straub T., Bender M. *J. Am. Chem Soc.* 1972, 94, 8875; Hirayama F., Utsuki T., et al., *J. Pharm. Sci.* 1992, 81, 817). The reaction rate increases when flexible guest molecules are forced to fix in a reactive conformation, and vice versa (Griffiths D., Bender M., *J. Am. Chem. Soc.* 1973, 95, 1679). The stoichiometry of cyclodextrin complexes affects chemical reactivies of guest drug molecules in a predictable way, and can thus be employed to exact a greater degree of precision and control to achieve the desired pharmacokinetics, onset of action, and peak concentration of guest cannabinoid drug molecules, and ultimately, the desired therapeutic effects in users who consume the present invention via oral administration.

Present Invention Improves Bioavailability of Cannabinoids

Finally, as set out above, available cannabinoid-based drugs have demonstrably poor bioavailability; only 5-20% of commercially-available Marinol®, and its API, dronabinol (THC), ever reach the blood plasma (National Academy of Sciences, Institute of Medicine. *Marijuana and Medicine: Assessing the Science Base.* (1999) p. 203; Growing L., et al. Therapeutic use of *Cannabis*: clarifying the debate. Drug and Alcohol Review (1998)). Thus there is a need for improved dosage forms of both natural and synthetic cannabinoids with superior bioavailability.

The present invention exploits the traits of cyclodextrins to overcome the shortcomings of commercially-available cannabinoid drugs. The rate and extent of a poorly water-soluble drug from its cyclodextrin complex can be optimized by adjusting various factors affecting the dissociation equilibrium of the complex, both in the formulation, as well as the biophase in which the complex is administered. In general, maximal absorption enhancement is obtained when just enough cyclodextrin is use to solubilize the drug in solution. Further addition of cyclodextrin to the drug solution decreases the free fraction of the drug and, hence, decreases the drug's bioavailability (Uekama K., supra.).

Hydrophilic cyclodextrins are particularly useful for improving stability, solubility, dissolution rate, and wettability of drugs through the formation of inclusion complexes (Uekama K., Hirayama F., et al. *Drug Targeting Delivery*: Boer, A G, Ed.; Harwood Publishers: Amsterdam, 1993; Vol. 3, p. 411). Hydrophilic cyclodextrins have been successfully employed to, as is the current need for cannabinoid-based drugs, develop rate- and/or time-controlled oral formulations (Uekama K., Cyclodextrin Drug Carrier Systems, supra.). They have been applied to enhance the oral bioavailability of steroids, cardiac glycosides, nonsteroidal anti-inflammatory drugs, barbiturates, antiepileptics, and vasodilators (Szejtli, J. *Cyclodextrins and Their Inclusion Complexes*; Aka-demiai Kiado: Budapest, 1982; *Cyclodextrins and Their Industrial Uses*; Duchene, D., Ed.; Editions de Sante: Paris, 1987; Szejtli, J. *Cyclodextrin Technology*; Kluwer: Dordrecht, The Netherlands, 1988; Uekama, K. *Yakugaku Zasshi* 1981, 101, 857; Szejtli, J. *J. Inclusion Phenom.* 1983, 1, 135; Pitha, J.; Szente, L.; Szejtli, J. *In Controlled Drug Delivery*; Bruck, S. D., Ed.; CRC: Boca Raton, Fla., 1983; p 125; *New Trends in Cyclodextrins and Derivatives*; Duchene, D., Ed.; Editions de Sante: Paris, 1991; Uekama, K. *Pharm. Int.* 1985, 6, 61). As such, hydrophilic cyclodextrins are ideally suited for the formulation of an sustained-release aspect of drug formulations, and is particularly well-suited for those APIs, e.g., dronabinol, which exhibit poor bioavailability and variability. The present invention, in one embodiment, seeks to employ the above properties of hydrophilic cyclodextrins in order to achieve layer of sustained-release cannabinoid, and thereby to achieve long lasting therapeutic effects (e.g., sleep-maintaining effects) in the user upon oral administration.

Additional Excipients for Sustained Release Layers

The silica gel, such as Syloid Xdp® (W.R. Grace & Co.), may be used herein as an adsorbant and solid carrier and should be selected for properties making it ideal for use with lipid formulations; able to adsorb large amounts of oils with a resulting density and flowability that is useful for maximum loading into tablets. It is also desirable that the oil will release from the silica gel without the use of additional surfactants.

Lecithin is a naturally occurring mixture of the diglycerides of stearic, palmitic, and oleic acids, linked to the choline ester of phosphoric acid, commonly called phosphatidylcholine. Hydrogenated Lecithin is the product of controlled hydrogenation of Lecithin. Bilayers of these phospholipids in water may form liposomes, a spherical structure in which the acyl chains are inside and not exposed to the aqueous phase. Lecithin and Hydrogenated Lecithin are used in a large number of cosmetic formulations as skin conditioning agents-miscellaneous and as surfactant-emulsifying agents. Hydrogenated Lecithin is also used as a nonsurfactant suspending agent. Lecithin is virtually nontoxic in acute oral studies, short-term oral studies, and subchronic dermal studies in animals. Lecithin is not a reproductive toxicant, nor is it mutagenic in several assays. Fiume Z. Int J Toxicol. 2001; 20 Suppl 1:21-45.

Soy lecithin one of the most widely used food additives on the market today. It is used as an emulsifier. It helps to emulsify numerous foods, even unlikely emulsions such as chocolate. In chocolate, lecithin stabilizes the cocoa butter fat so it doesn't separate from the moisture, cocoa solids and dairy.

Lecithin also extends shelf life by stabilizing emulsions, and it also reduces "stickiness" and is often used as a "releasing agent."

Chemically, glyceryl behenate, such as Compritol 888® (Gattefosse SAS), is a mixture of various esters of behenic acid and glycerol (glycerides). The mixture predominately contains the diester glyceryl dibehenate. 21 C.F.R. 184.1328. Glyceryl behenate is a tablet and capsule lubricant and a lipidic coating excipient. It has been used for the encapsulation of various drugs such as retinoids. It has also been used as a matrix-forming agent for the controlled release of water-soluble drugs and as a lubricant in oral solid dosage formulations. It is also used widely as ingredient for preparation of lipidic nano-particles such as solid lipid nanoparticles (SLN) and nanostructured lipid carriers (NLC). Handbook of pharmaceutical excipient, 5th edition.

Peg-6 caprylic/capric glycerides (Labrasol) is a polyethylene glycol derivative of a mixture of mono-, di-, and triglycerides of caprylic and capric acids with an average of 6 moles of ethylene oxide. It is used in the present invention as an emulsifying agent. A preferred form is caprylocaproyl macrogol-8 glycerides, a non-ionic water dispersible surfactant composed of polyethylene glycol (PEG) esters, a glyceride fraction, and free PEG. This form is able to self-emulsify on contact with aqueous media to form a fine micro-emulsion. It is a solubilizer and wetting agent: its surfactive power improves the solubility and wettability of active pharmaceutical ingredients in vitro and in vivo. See for example, www.Gattefosse.com, accessed Mar. 5, 2017.

Hydroxypropyl methylcellulose (HPMC), which is water soluble, behaves as a swellable absorptive polymer in the limited volumes of aqueous media in the gastrointestinal tract. Drug dispersed in this polymer, as in the monolithic tablets of the instant invention, diffuses through the viscous hydrated polymer at a rate dependent on the movement kinetics of the polymer chains. The faster these relax, the faster the diffusion rate.

Hydrophilic polymers like HPMC also control drug release by erosion mechanisms. After consumption of the dosage form, the GI tract fluid encounters the dosage unit, causing the polymer to hydrate and swell. Weakened mechanical properties in the swollen state may cause the hydrated polymer to break away from the prime particle (compact or pellet). Drug release may therefore be controlled by a combination of diffusion and erosion. Such release mechanisms can apply to systems where drug is dispersed in or coated with polymer.

Microcrystalline cellulose, found in Prosolv® (Penwest Pharmaceuticals), is derived from refined wood pulp and may be used in the present invention as an anti-caking agent and emulsifier.

Microcrystalline cellulose (MCC) is pure partially depolymerized cellulose synthesized from α-cellulose precursor. The MCC can be synthesized by different processes such as reactive extrusion, enzyme mediated, steam explosion and acid hydrolysis. The later process can be done using mineral acids such as H2SO4, HCl and HBr as well as ionic liquids. The role of these reagents is usually to destroy the amorphous regions remaining in the crystalline domains. The degree of polymerization is typically less than 400. The MCC particles with size lower than 5 μm not be more than 10%. The MCC is a valuable additive in pharmaceutical, food, cosmetic and other industries. Different properties of MCC are measured to qualify its suitability to such utilization, namely particle size, density, compressibility index, angle of repose, powder porosity, hydration swelling capacity, moisture sorption capacity, moisture content, crystallinity index, crystallite size and mechanical properties such as hardness and tensile strength. See Wikipedia link: "en.wikipedia.org/wiki/Microcrystalline cellulose". Accessed Sep. 16, 2016.

Microcrystalline cellulose is a naturally occurring polymer, it is composed of glucose units connected by a 1-4 beta glycosidic bond. These linear cellulose chains are bundled together as microfibril spiralled together in the walls of plant cell. Each microfibril exhibits a high degree of three-dimensional internal bonding resulting in a crystalline structure that is insoluble in water and resistant to reagents. There are, however, relatively weak segments of the microfibril with weaker internal bonding. These are called amorphous regions. The crystalline region is isolated to produce microcrystalline cellulose. en.wikipedia.org/wiki/Microcrystalline cellulose. Accessed Sep. 16, 2016.

Colloidal silicon dioxide, found in Prosolv® (Penwest Pharmaceuticals), or silicon dioxide may be used in the instant invention as an anti-caking agent, adsorbent, disintegrant, and glidant to allow powder to flow freely when tablets are processed.

Hydroxypropylcellulose (HPC), such as Klucel® (Hercules Incorporated), is an ether of cellulose in which some of the hydroxyl groups in the repeating glucose units have been hydroxypropylated. In the instant invention it may be used as a tablet binder and emulsifier.

In a further aspect, the present invention may employ a separate or additional modified- or delayed-release layer. An enteric preparation can be classified as time-controlled release, since the drug is preferentially released in the intestinal tract. Hydrophobic excipients having a weak acidic group are preferable because they are less soluble in water at low pH, but soluble in neutral and alkaline regions due to the ionization of the acidic group (Uekama K., Cyclodextrin Carrier Systems, supra.). Under the control of this pH dependence, the delayed release dosage form which passes from the stomach into the higher pH environment of the upper small intestine would experience increased drug release (Ibid.).

A modified release dosage form may be formulated as a tablet or multiparticulate which may be encapsulated. Other modified release dosage forms known in the art can be employed in different layers of the instant invention. In certain embodiments, the combination of therapeutic agents may be formulated to provide for an increased duration (sustained release) of therapeutic action.

The modified release formulations according to the instant invention have many advantages, including reduction of administration/dosage frequency, prolonged drug efficacy, and avoidance of toxicity associated with administration of a simple plain tablet (Uekama K., Cyclodextrin Carrier Systems, supra.). For this purpose, hydrophobic cyclodextrins, such as alkylated and acylated derivatives, are useful as slow release carriers for water-soluble drugs. This aspect of drug delivery is ideal for the cannabinoids of the instant invention where the release rate is markedly retarded via complexation of the cannabinoid with acylated or hydroxylated cyclodextrins, thereby sustaining sufficient drug levels over long periods of time (Uekama K., Korikawa T., et al. J. Pharm. Pharmacol. 1994, 46, 714). This is particularly useful for, in one embodiment, the application of the present invention to treat sleep disorders, where prolonged drug action is necessary over a period of 8 hours or longer.

Cyclodextrins improve the bioavailability and release rate of the cannabinoid via a prominent retarding effect. It presents significant advances over commercially-available cannabinoid based drugs in terms of bioavailability, pharmacokinetics, solubilization, and stability, and is thereby a superior vehicle for attaining desired therapeutic effects in users over desired therapeutic windows.

The sustained release formulations of the present invention represent a significant improvement over existing drug formulations of cannabinoids.

Immediate Release Layer

The present invention, is further directed to an immediate-release drug composition layer comprising an fast release matrix layer comprising cannabidiol containing granules and extragranular excipients wherein the granules comprise:

cannabidiol;
dibasic calcium phosphate;
lactose monohydrate;
pregelatinized modified starch; and
hydroxyl ethyl cellulose; and where the extragranular excipients comprise about;
carbomer homopolymer;
polyethylene oxide;
hypromellose; and
methacrylic acid copolymer.

This immediate-release layer presents a significant advantage over commercially available Marinol® for example, with its onset of action of between 1 h and 4 h. In this embodiment, the fast or even immediate release layer would, upon oral administration, readily dissolve in the gastrointestinal tracts, resulting in an enhancement of bioavailability of otherwise poorly water-soluble dronabinol.

Matrix-based formulation systems may incorporate monolithic matrix systems or coating systems. Monolithic matrix systems include a polymer matrix containing dispersed or dissolved drug. Either hydrophilic or insoluble matrix systems may be used. Coated systems include a drug-containing core enclosed within a polymer barrier coat. These coating systems can be simple diffusion/erosion systems or osmotic systems where the drug core is contained within a semipermeable polymer membrane with a mechanical/laser drilled hole for drug release, driven by osmotic pressure generated within the tablet core.

Drug embedded matrix tablets are one of the least complicated approaches for obtaining high bioavailability dosage forms and are widely used and preferred when achievable. Polymers and release retarding materials used as matrix formers in matrix tablets play a vital role in controlling the drug release from the tablets. Though a variety of polymeric materials are available to serve as release controlling matrix materials, there is a continued need to develop new, safe and effective release modifying matrix dosage forms for preparing simple matrix tablets or tablet layers for improved release and bioavailability. The immediate release formulation layers of the present invention represent a significant improvement over existing cannabinoid formulations.

Granule Ingredients
Cannabinoids
Starch acetate

A key aspect of this invention is its unique combination of rate controlling polymers and modified starch which is acid digestion resistant and remains undigested in the acidic region of stomach and intestine so that it holds the drug content and improves bioavailability.

Starch acetate as a rate controlling polymer has recently been studied but the specific combination of pregelatinized starch acetate with rate controlling polymers of the present invention allow an improved immediate release drug delivery system of cannabidiol or other cannabinoid in a monolithic matrix tablet to simply and cost effectively improve on the inadequate delivery systems currently employed.

Starch is a natural polymer which possesses many unique properties. Some synthetic polymers are biodegradable and can be tailor-made easily. Therefore, by combining the individual advantages of starch and polymers, starch-based completely biodegradable polymers are useful for the present invention.

Starches are also used in the food manufacturing industry for processing, and as food thickeners or stabilizers. There are many other diverse uses for starches in the manufacturing industry.

Starch is regenerated from carbon dioxide and water by photosynthesis in plants. Owing to its complete biodegradability, low cost and renewability, starch is considered as a promising candidate for developing sustainable materials. In view of this, starch has been receiving growing attention since the 1970s. Only in the last few years has starch received attention by drug formulators.

Starch is mainly composed of two homopolymers of D-glucose: amylase, a mostly linear α-D(1,4')-glucan and branched amylopectin, having the same backbone structure as amylose but with many α-1,6'-linked branch points. Starch chains have a lot of hydroxyl groups, including two secondary hydroxyl groups at C-2 and C-3 of each glucose residue, as well as one primary hydroxyl group at C-6 when it is not linked. The available hydroxyl groups react with alcohols: they can be oxidized and reduced, and may participate in the formation of hydrogen bonds, ethers and esters.

Starch has different proportions of amylose and amylopectin ranging from about 10-20% amylose and 80-90% amylopectin depending on the source. Amylose is soluble in water and forms a helical structure. Starch occurs naturally as discrete granules since the short branched amylopectin chains are able to form helical structures which crystallize. Starch granules exhibit hydrophilic properties and strong inter-molecular association via hydrogen bonding formed by the hydroxyl groups on the granule surface.

Starches are used in the pharmaceutical industry for a variety of uses, such as an excipient, a tablet and capsule diluent, a tablet and capsule disintegrant, a glidant, or as binder. Starches also absorb water rapidly, allowing tablets to disintegrate appropriately. Dave R H. Overview of pharmaceutical excipients used in tablets and capsules. Drug Topics (online). Advanstar. Oct. 24, 2008 drugtopics.modernmedicine.com/drugtopics/Top+News/Overview-of-pharmaceutical-excipients-used-in-tabl/ArticleStandard/Article/detail/561047. Accessed Mar. 5, 2017.

Modified starches have been used for various pharmaceutical purposes such as fillers, superdisintegrants and matrix formers in capsules and tablet formulations. Starch-based biodegradable polymers, in the form of microsphere or hydrogel, are suitable for drug delivery. Crosslinked starch glycolate (sodium salt) is an anionic polymer and produced by crosslinking and carboxymethylation of potato starch. In contrast to the starch of the present invention, in the state of the pharmaceutical art, the sodium starch glycolate from potato is preferred. Crosslinked starch glycolate is used in more than 155 drugs in the US market including Primojel® (DMV-Fonterra) Acyclovir (Zovirax®); theophylline (Theo-Dur®); diltiazem (Cardizem® LA); cimetidine (Tagamet®); fenofibrate (Lipofen®); metoprolol tartrate (Lopressor®) mH. Omidian and K. Park in Juergen Siepmann 1 Ronald A. Siegel Michael J. Rathbone Editors Fundamentals and Applications of Controlled Release Drug Delivery.

Raw starch does not form a paste with cold water and therefore requires cooking if it is to be used as a food thickening agent. Pregelatinized starch, mostly from maize, has been cooked and dried. Pregelatinized starches are highly digestible. Used in instant puddings, pie fillings, soup mixes, salad dressings, sugar confectionery, and as a binder in meat products. Nutritional value is the same as that of the original starch. The result is a multipurpose excipient combining the dilution and disintegration power of native starch with new functionalities, such as flowability and controlled cohesive power. Pregelatinized starches are preferred for the present invention. David A Bender. Starch, Pregelatinized. A Dictionary of Food and Nutrition. 2005. Retrieved from Encyclopedia.com.

One of the important modifications of starch is acetylated starch. Starch acetate has excellent bond forming ability and has been used in the food industry extensively. One method of synthesizing starch acetate is to mix and reflux for 5 h at 150° C. plant starch, excess acetic anhydride and sodium hydroxide 50% solution. The reaction mixture is added to cold water to precipitate the starch acetate formed. The product is collected by vacuum filtration, washed repeatedly with water and dried at 80° C. for 2 h. Starch acetate may be characterized by determining the extent of acetylation and degree of substitution and by IR spectra. Solubility characteristics may also be tested.

Recently, starch acetate was synthesized, characterized and evaluated as rate controlling matrix former for controlled release nifedipine. Matrix tablets of nifedipine were formulated employing starch acetate in different proportions of drug and polymer and the tablets were evaluated for drug release kinetics and mechanism. Nifedipine is an effective and widely prescribed antianginal drug that requires controlled release owing to its short biological half-life of 2.5 h. A few sustained release formulations of nifedipine are available commercially. Starch acetate was found suitable as matrix former for controlled release and the matrix tablets of nifedipine formulated employing starch acetate gave controlled release of nifedipine over 24 h and fulfilled the official release specification of nifedipine extended release tablets. Synthesis, Characterization And Evaluation Of Starch Acetate As Rate Controlling Matrix Former For Controlled Release Of Nifedipine Chowdary and Radha *Int. J. Chem. Sci.:* 9(2), 2011, 449-456.

Starch acetate is insoluble in water, aqueous buffers of pH 1.2 and 7.4, methanol, petroleum ether, dichloromethane and cyclohexane. It is freely soluble in chloroform.

Starch acetates have mostly been investigated as film-forming coatings using starch acetates (DS 2.8) in combination with commonly used plasticizers on the physical properties of starch acetate films have been evaluated. Starch acetate films are tougher and stronger than ethylcellulose films at the same plasticizer concentration. Also, in most cases, the water vapor permeability of starch acetate films was lower than that of ethylcellulose films. Due to the good mechanical properties, low water vapor, and drug permeabilities of the films, starch acetate seems to be a promising film-former for pharmaceutical coatings. The toughness of the films may result from their dense film structure, which is due to strong interaction forces between adjacent SA molecular chains. J Pharm Sci. 2002 January; 91(1):282-9. Starch acetate—a novel film-forming polymer for pharmaceutical coatings. Tarvainen M, Sutinen R, Peltonen S, Tiihonen P, Paronen P.

Deformation during powder volume reduction, strain-rate sensitivity, intrinsic elasticity of the materials, and tensile strength of the tablets have been examined with the use of starch acetate powders as tablet excipients. Starch acetate with the lowest degree of substitution (ds) still possessed characteristics of native starch granules. The properties of more highly substituted starch acetates depend on precipitation and drying processes. The acetate moiety, perhaps in combination with existing hydroxyl groups, is an effective bond-forming substituent. The formation of strong molecular bonds leads to a very firm and intact tablet structure. Some fragmentation is induced by the slightly harder and more irregular shape of high-substituted starch acetate particles. The plastic flow under compression is enhanced.

Acetylated materials are slightly less sensitive to fast elastic recovery in-die, but somewhat more elastic out-of-die. In spite of their superior bonding, starch acetates under compression behave similarly to native starches. Drug Dev Ind Pharm. 2002; 28(2):165-75. Acetylation enhances the tabletting properties of starch. Raatikainen P, Korhonen O, Peltonen S, Parone P.

Agglomeration of powders containing starch acetate prior to tablet compression allows for modification and control of the release rate of the drugs from the starch acetate matrix tablets as well as the tensile strength of the tablets. J Pharm Sci. 2007 February; 96(2):438-47. Modifying drug release and tablet properties of starch acetate tablets by dry powder agglomeration. Maki R, Suihko E, Rost S, Heiskanen M, Murtomaa M, Lehto V P, Ketolainen J.

Other Granule Excipients

Lactose is a milk sugar. It is a disaccharide composed of one galactose and one glucose molecule. In the pharmaceutical industry, lactose is used to help form tablets because it has excellent compressibility properties. It is also used to form a diluent powder for dry-powder inhalations. Lactose may be listed as lactose hydrous, lactose anhydrous, lactose monohydrate, or lactose spray-dried.

Various calcium phosphates are used as diluents in the pharmaceutical industry. Diluents are added to pharmaceutical tablets or capsules to make the product large enough for swallowing and handling, and more stable. Some calcium phosphate salts can be anhydrous, meaning the water has been removed from the salt form. Other calcium phosphates are termed dibasic, meaning they have two replaceable hydrogen atoms.

Hydroxypropyl cellulose (HPC) is a nonionic polymer, being a partially substituted poly (hydroxypropyl) ether of cellulose. It is available in different grades with differing solution viscosities. Molecular weight ranges from ~80,000 to 1,150,000. High viscosity grades of HPC are generally used. Inclusion levels can vary from 15 to 40%. Addition of an anionic surfactant (e.g., sodium lauryl sulfate) reportedly increases HPC viscosity and as a consequence reduces drug release rate. Combinations of HPC and other cellulosic polymers have been used to improve wet granulation and tableting characteristics and better control of drug release. HPC is thermoplastic and its presence may enable processing of HPMC containing formulations using hot melt extrusion or injection molding. It is not widely used because of its low swelling capacity and sensitivity to ionic strength of the dissolution media. Gel strengths of HPC matrices decrease during dissolution, leading to less cohesive gel structures. The lower tablet gel strength of HPC matrices, compared to HPMC can cause poor in vitro/in vivo correlation.

Hydroxyethyl cellulose (HEC) is also a nonionic, partially substituted poly (hydroxyethyl) ether of cellulose. It is available in several grades from Ashland Aqualon Functional Ingredients under the brand name of Natrosol®. These vary in viscosity and degree of substitution. High viscosity grades of HEC (1,500-5,500 mPa of 1% solution) are sometimes used in extended release formulations. Typical inclusion levels are 15-40% of the total formulation mass. However, it may be used in much lower levels such as the 2-3% used in the formulation of certain examples of this invention. Swelling of HEC matrices has been reported to be considerably greater than HPC matrices. HEC matrices also exhibited relatively higher erosion rates, t50% (time to 50% release) being shorter for HEC than for HPC matrices.

Extra Granular Excipients

Gelling Agents

A carbomer is a homopolymer of acrylic acid, which is cross-linked, or bonded, with any of several polyalcohol allyl ethers. Carbomer is a generic name for synthetic high molecular weight polymers of acrylic acid. They may be homopolymers of acrylic acid, crosslinked with an allyl etherpentaerythritol, allyl ether of sucrose or allyl ether of propylene. In a water solution at neutral pH, carbomer is an anionic polymer. This makes carbomers polyelectrolytes, with the ability to absorb and retain water and swell to many times their original volume.

Poly acrylic acid and its derivatives are used in disposable diapers, ion exchange resins and adhesives. They are also popular as thickening, dispersing, suspending and emulsifying agents in pharmaceuticals, cosmetics and paints. Usually appearing as a white powder, the compound is used as a thickener and emulsion stabilizer. Best known for its use in the cosmetic industry, it also has practical applications in medicine and hygiene. wikipedia.com and wisegeek.com. Accessed Mar. 5, 2017.

Similar to other polymers, carbomers are made of long chains of many smaller, repeating molecules, which have a large number of bonds. Although the molecular weight varies based on the exact molecules found in the chain, it typically is relatively high. These compounds are capable of absorbing large amounts of water, increasing in volume up to 1,000 times in some cases, so they can form gels and thick solutions that are stable and resistant to spoilage.

Scientists are able to make different types of carbomers, each of which has a slightly different molecular structure. To keep these different kinds straight, they use a numerical suffix and capitalize the word as in a proper title or name, such as Carbomer 940. Under this labeling system, the number indicates the average molecular weight of the polymer chains.

Carbomers are available from Lubrizol under the brand name of Carbopol® and are available in grades that vary in viscosity, polymer type, and polymerization solvent. Being cross-linked, these polymers are not water soluble but are swellable and gel forming. Swelling and gel formation behaviors differ somewhat from other hydrophilic polymers like HPMC, where swelling follows polymer hydration, leading to relaxation of polymer chains and their subsequent entanglement (physical crosslinking) to form a viscous gel. With acrylic acid polymers, surface gel formation is not due to polymer chain entanglement (the polymers are already cross-linked) but to formation of discrete micro gels comprising many polymer particles. Erosion, as occurs with linear polymers like HPMC does not occur because of the water insolubility. Instead, when the hydrogel is fully hydrated, osmotic pressure from within breaks up the structure, sloughing off discrete pieces of the hydrogel. The hydrogel remains intact and drug continues to diffuse uniformly through the gel layer.

In contrast to the situation with linear polymers, higher viscosity does not result in slower drug release with cross-linked polymers. Lightly cross-linked polymers (lower viscosity) are generally more efficient in controlling release than highly cross-linked variants. Release from carbomer matrices may depend on the pH of dissolution media, because of the anionic nature of the polymer (pKa 6±0.5). Swelling and gel formation are pH dependent. At lower pH the polymer is not fully swollen and drug release is faster. As pH increases the polymer swells and rapidly forms a gel layer, prolonging drug release. Carbomers, being anionic may form complexes with cationic drugs depending on drug properties such as pKa, solubility, amine group strength, steric orientation, molecular weight and size.

It has been reported that carbomer inclusion levels of about 30% produce comparable drug release profiles to HPMC in both water and 0.1 N HCl. Release was slower in pH 6.8 phosphate buffer. Carbomer matrices also exhibited significantly lower gel strengths compared to HPMC matrices in all three media. This has been postulated as the reason for their significantly faster drug release in vivo compared to HPMC matrices. 7 Drug-Polymer Matrices for Extended Release 143.

Polyethylene oxide (PEO) [POLYOX™] resins are water soluble, nonionic polymers manufactured by Dow Chemical Company. They are free flowing white powders, soluble in water at temperatures up to 98° C. and in certain organic solvents. Structures comprise the repeating sequence—(CH2CH2O)n where n represents the average number of oxyethylene groups. It is highly crystalline and available in molecular weight grades ranging from 1×105 to 7×106 Da. Their high molecular weights mean that the concentration of reactive end groups is very low. However, as their paired ether-oxygen electrons have a strong affinity for hydrogen bonding, they can form association complexes with a variety of monomeric and polymeric electron acceptors (e.g., gelatin, carbomer) as well as certain inorganic electrolytes, e.g., alkali halides. These water-soluble resins have applications in pharmaceutical products, such as in controlled release solid dose matrix systems, tablet binding, tablet coatings, transdermal drug delivery systems, and mucosal bioadhesives and gastro-retentive dosage forms. They exhibit film forming and water retention properties. It has high water solubility and low toxicity. www.pharmainfo.net/reviews/polyox-polyethylene-oxide-applications-pharma-industry. Submitted by Saritha R Bhandary on Wed, Sep. 22, 2010-22:38. Accessed Mar. 5, 2017.

PEO resins are among the fastest hydrating water soluble polymers, quickly forming hydrogels that initiate and regulate drug release. Systems using such resins are often superior in approaching zero-order release profiles. PEO is generally used at 20-90% inclusion level depending on the drug and the desired release characteristics, however, in the instant invention levels of 10% and less are generally used.

PEO behaves similarly to HPMC in hydrophilic matrix systems. With appropriate selection of a suitable viscosity grade, one is able to achieve release profiles similar to hypromellose matrices. Grades available are POLYOX WSR-205 NF, WSR-1105 NF, WSR N-12 K NF, WSR N-60 K NF, WSR-301 NF, WSR-303 NF, and WSR Coagulant NF. The high swelling capacity of PEO has been used in hydrophilic matrices to achieve expanded swelling, providing enhanced gastroretention.

Several other materials can be useful gel matrix formers. They include methylcellulose, guar gum, chitosan, and cross-linked high amylose starch.

Hydroxypropyl methylcellulose (HPMC or hypromellose), such as Methocel® (Dow Chemical Co.) is a semi-synthetic, inert, viscoelastic polymer used as an ophthalmic lubricant, as well as an excipient and controlled-delivery component in oral medicaments, found in a variety of commercial products. Hypromellose is a solid, and is a slightly off-white to beige powder in appearance and may be formed into granules. The compound forms colloids when dissolved in water. Wikipedia.com. It is widely used in matrix applications. Key advantages include global regulatory acceptance, stability, nonionic nature (resulting in pH-independent release of drugs), and ease of processing by direct compression (DC) or granulation. Other advantages are versatility and suitability for various drugs and release profiles (different viscosity grades being available) and extensive history of use. It is a mixed alkyl hydroxyalkyl cellulose ether containing methoxyl and hydroxypropyl groups. Type and distribution of the substituent groups affect physicochemical properties such as rate and extent of hydration, surface activity, biodegradation, and mechanical plasticity. Matrices exhibit pH-independent drug release profiles while aqueous solutions are stable over a wide pH range and are resistant to enzymatic degradation. Controlled Release in Oral Drug Delivery Clive G. Wilson Crowly Springer 2011 Chapter 7Drug-Polymer Matrices for Extended Release Sandip B. Tiwari, James DiNunzio, and Ali Rajabi-Siahboomi.

The first two digits represent the mean % methoxyl substitution and the last two the mean % hydroxypropyl substitution. HPMC is highly hydrophilic, hydrating rapidly in contact with water. Since the hydroxypropyl group is hydrophilic and the methoxyl group is hydrophobic, the ratio of hydroxypropyl to methoxyl content influences water mobility in a hydrated gel layer and therefore, drug release. Grades for extended release matrix formulations include E50LV, K100LV CR, K4M CR, K15M CR, K100M CR, E4M CR, and E10M CR.Viscosities of 2% aqueous solutions of these polymers range from 50 to 100,000 cPs at 20° C. Inclusion level can vary from 10 to 80% dosage form.

Hydroxypropyl methylcellulose (HPMC or hypromellose), such as Methocel® (Dow Chemical Co.) is a semi-synthetic, inert, viscoelastic polymer used as an ophthalmic lubricant, as well as an excipient and controlled-delivery component in oral medicaments, found in a variety of commercial products. Hypromellose is a solid, and is a slightly off-white to beige powder in appearance and may be formed into granules. The compound forms colloids when dissolved in water. Wikipedia.com. It is widely used in matrix applications. Key advantages include global regulatory acceptance, stability, nonionic nature (resulting in pH-independent release of drugs), and ease of processing by direct compression (DC) or granulation. Other advantages are versatility and suitability for various drugs and release profiles (different viscosity grades being available) and extensive history of use. It is a mixed alkyl hydroxyalkyl cellulose ether containing methoxyl and hydroxypropyl groups. Type and distribution of the substituent groups affect physicochemical properties such as rate and extent of hydration, surface activity, biodegradation, and mechanical plasticity. Matrices exhibit pH-independent drug release profiles while aqueous solutions are stable over a wide pH range and are resistant to enzymatic degradation. Controlled Release in Oral Drug Delivery Clive G. Wilson Crowly Springer 2011 Chapter 7Drug-Polymer Matrices for Extended Release Sandip B. Tiwari, James DiNunzio, and Ali Rajabi-Siahboomi.

In addition to its use in ophthalmic liquids, hypromellose can be used as an excipient in oral tablet and capsule formulations, where, depending on the grade, it functions as controlled release agent to control the release of a medicinal compound into the digestive tract. It is also used as a binder and as a component of tablet coatings.

Polymethacrylates are synthetic cationic or anionic polymers of dimethylaminoethyl methacrylates, methacrylic acid, and methacrylic acid esters in varying ratios. Methacrylic acid is a colourless, viscous organic acid with an acrid unpleasant odor. It is soluble in warm water and miscible with most organic solvents. Methacrylic acid is produced industrially on a large scale as a precursor to its esters, especially methyl methacrylate (MMA) and poly(methyl methacrylate) (PMMA). The methacrylates have numerous uses, most notably in the manufacture of polymers with trade names such as Lucite and Plexiglas. MAA occurs naturally in small amounts in the oil of Roman chamomile. Several types are commercially available (Eudragits®, Evonik) for use in drug formulations as dry powders and aqueous dosage forms. Polymethacrylates can be used as binders for both aqueous and organic solvent granulation, forming matrices with extended release characteristics. In general, greater polymer inclusion levels (5-20%) are used to control release from matrices. Drug release may also be affected by pH of the dissolution medium. Wiki.

Lubricants

Magnesium stearate is used as an anti-adherent and it has lubricating properties, preventing the ingredients from sticking to manufacturing equipment during the compression of powders into solid tablets. Magnesium stearate may also affect the release time of the cannabidiol in the tablets.

Coating

Opadry is A one-step film coating system which combines polymer, plasticizer and pigment. Opadry film coating results in attractive, elegant coatings that can be easily dispersed in aqueous or organic solvent solutions. Opadry results in the elimination of separate inventories of polymer, plasticizer and pigment and reduces batch-to-batch color inconsistency.

The fast or even immediate release layer overcomes the shortcomings of currently commercially available cannabinoid-based drugs (e.g., Marinol® onset of 1 h to 4 h, variability) while avoiding the adverse effects of extended psychoactivity (i.e. avoidance of a "THC tail" by ensuring use of all dronabinol within a specified therapeutic window).

In certain other embodiments, the fast or even immediate release layer may be further comprised of ingredients in order to assist with achieving desired therapeutic effects in the short term. In one embodiment, the formulation may be directed at the improvement of sleep ("sleep aid formulation"). In such an embodiment of the present invention, the fast or even immediate release layer may contain twenty-five (25.0) mg of dronabinol, in powder form or in the form of cannabinoid resin, as well as the following herbal ingredients, which contain sedative properties: one hundred (100.0) mg of L-Theanine, sixty two-and-a-half (62.5) mg of Skullcap Herb (*Scutellaria lateriflora* L.), one hundred (100) mg of *Rhodiola* (*Rhodiola rosea* L.), and five (5.0) mg of Chamomile Flower (*Matricaria Recutita*).

In the present invention, the matrix-based sustained release systems may incorporate coating systems. Coated systems include a drug-containing core enclosed within a polymer barrier coat. These coating systems can be simple diffusion/erosion systems or osmotic systems where the drug core is contained within a semipermeable polymer membrane with a mechanical/laser drilled hole for drug release, driven by osmotic pressure generated within the tablet core. All of these technologies may be employed in certain embodiments of the present invention.

Drug embedded matrix tablets are one of the least complicated approaches for obtaining controlled release and are widely used and preferred when achievable. Polymers and release controlling materials used as matrix formers in matrix tablets play a vital role in controlling the drug release from the tablets. Though a variety of polymeric materials are available to serve as release retarding matrix materials, there is a continued need to develop new, safe and effective release modifying matrix materials and formulas for preparing simple matrix tablets for controlled release.

Although the following examples illustrate the practice of the present invention in its embodiments, the examples should not be construed as limiting the scope of the invention. Other embodiments will be apparent to one of skill in the art from consideration of the specifications.

EXAMPLES

Example 1: Immediate Release Layer (Aspect of Single-, Bi-, or Tri-Layer Tablet)

In this example, fast or even immediate release cannabinoid in accordance with the present invention is prepared having the formula listed in Table 1:

TABLE 1

| Item No. | Ingredient | Function |
|---|---|---|
| 1 | Cannabinoid extract | API |
| 2 | Dibasic Calcium Phosphate Dihydrate (Emcompress ® Premium), NF | Pharmaceutical excipient Diluent |
| 3 | Lactose Monohydrate (Granulac-200), NF | Pharmaceutical excipient Diluent |
| 4 | Pregelatinized Modified Starch (Amprac-01), NF | Binder |
| 5 | Hydroxy Ethyl Cellulose (Natrosol ® 250 HHX Pharm), NF | Binder |
| 6 | Purified Water# | |
| 7 | Carbomer Homopolymer, Type A (Carbopol ® 71 G Polymer), NF | Release controlling agent |
| 8 | Polyethylene Oxide (Sentry (TM) Polyox (TM) WSR Coagulant-Leo), NF | Release controlling agent |
| 9 | Hypromellose (Benecel ® K200M PH CR), NF | Release controlling agent |
| 10 | Methacrylic Acid Copolymer, Type C (Eudragit ® L 100-55), NF | Release controlling agent |
| 11 | Magnesium Stearate, NF | Lubricant |
| | TOTAL | |
| 12 | Opadry II White (85F18422), INH | Film Coating Material |
| 13 | Purified Water#, USP | Coating Solvent |

Certain drug formulation layers of the present example are prepared as follows:

Granulating: the cannabinoid is blended with hydroxy ethyl cellulose, dicalcium phosphate, lactose monohydrate and pregelatinized starch acetate in a high shear granulator. The mixture is then granulated in hot water and dry mixed with the granulator and impeller set at slow speed. With the granulator and impeller set a slow speed, purified water is added to the mixed powders and granulated with the granulator and impeller set at slow speed.

Drying: The wet granulation is transferred to a fluid bed dryer and dried.

Mixing: After being dried in a fluid bed dryer, the granules thus formed are mixed with carbomer homopolymer, polyethylene oxide, hypromellose, methacrylic acid copolymer.

Example 2: Sustained-Release Layer—Ingredients Useful for 25 mg Cannabinoid Tablet (Total 287.70 mg) Components (Aspect of Single, Bi- or Tri-Layer Tablet)

(1) Granules—229.0 mg granules

| | |
|---|---|
| beta-cyclodextrin | 150.0 mg |
| Sesame Oil | 25.0 mg |
| Cannabinoid Resin | 25.0 mg |
| Compritol 888 | 4.0 mg |

-continued

| | |
|---|---|
| Soy Lecithin | 2.5 mg |
| Labrasol | 22.5 mg |

(2) Blend

| | |
|---|---|
| Syloid XDP 3150 | 2.5 mg |
| Klucel LF Pharm | 5.0 mg |
| ProSolv90 | 25.0 mg |
| HPMC LVCR K100 | 12.5 mg |

Example 3: Formulation Methods for Sustained-Release Layer

The formulation according to the present example may be prepared as follows:
1. mix cyclodextrin with water for approximately 2.5 hours to form a slurry;
2. mix a cannabinoid resin and sesame oil together at a temp of about 60° C. until a uniform mixture is obtained;
3. add the uniform mixture or resin and oil to the cyclodextrin slurry and mix for about 1 hour;
4. mix soy lecithin and water together at a temperature of about 60° C., until a uniform slurry mixture is obtained;
5. slowly sprinkle the glyceryl behenate on to the resin, cyclodextrin mixture obtained in step 3 and mix for about 15 minutes;
6. slowly add the soy lecithin slurry to the mixture obtained in step 5 while increasing the mixer speed to achieve a uniform mixture;
7. slowly add Labrasol to the mixture obtained in step 6 while maintaining the uniform mixture;
8. continue mixing until a uniform mixture is obtained and being careful to not over mix;
9. transfer the mixture to stainless steel (or other suitable) trays;
10. place in an oven and dry at about 70° C. until the moisture content is less than 2.0% to form granules;
11. screen the granules through a 30 mesh;
12. screen each of the silica gel, hydroxypropylcellulose, microcrystalline cellulose/colloidal silicon dioxide, and hydroxypropylmethylcellulose together with through a 30 mesh;
13. add the resin granules and blend for about 10 minutes.

Example 4: Immediate-Release Layer in Conjunction with Additional APIs

In certain other embodiments, the fast or even immediate release layer may be further comprised of ingredients in order to assist with achieving desired therapeutic effects in the short term. In one embodiment, the formulation may be directed at the improvement of sleep ("sleep aid formulation"). In such an embodiment of the present invention, the fast or even immediate release layer may contain twenty-five (25.0) mg of dronabinol, in powder form or in the form of cannabinoid resin, as well as the following herbal ingredients, which contain sedative properties: L-Theanine, Skullcap Herb (*Scutellaria lateriflora* L.), Rhodiola (*Rhodiola rosea* L.), and Chamomile Flower (*Matricaria Recutita*).

Example 5: Sustained-Release Composition Layer in Conjunction with Additional APIs In this example, delayed release is achieved by coating single, bi- or tri-layer tablets comprising a cannabinoid along with a therapeutically effective amount of additional APIs such as metformin HCl or melatonin.

Example 6: Modified-Release Composition in Conjunction with Additional APIs

In one aspect of this modified-release formulation, cannabinoid APIs (e.g., cannabidiol) are combined with therapeutically effective amounts of other APIs, for example five (5.0) mg melatonin for use as a sleep aid, or fifty (50.0) g sertraline (Zoloft®) for additive anxiolytic and antidepressant effects, in conjunction with cannabidiol, for use in treating major depressive disorders and other depressive or psychological disorders. Such embodiments may include a cannabinoid fast or even immediate release layer of dronabinol or THC extract, for immediate sedative effect, along with the sustained release of cannabidiol for inhibitory effects on the undesirable "THC grogginess tail" associated with an extended therapeutic window for administration.

Example 7: Immediate-Release Layer (Aspect of Single, Bi- or Tri-Layer Tablet)

In certain embodiments, the present invention comprises a fast or even immediate release layer. An amorphous cannabinoid powder (e.g, dronanibinol) is prepared by spray-drying with 2-hydroxypropyl-β-cyclodextrin and a nonionic detergent HCO-60 is employed as a fast-release portion in order to attain an initial rapid dissolution and to prevent crystal growth during storage. The cannabinoid may also be in the form of cannabinoid resin (e.g., dronabinol resin).

Example 8: Tablet Coating

The tablets made according to the previous examples may be coated with Opadry II White and other coating agents (e.g., talc and titanium dioxide) to produce the final Tablets.

Example 9: Method of Treating Addiction

The tablets made according to the previous examples may be used to treat nicotine, alcohol, cannabis, cocaine, opioid, and other forms of addiction. In the present invention acute symptoms can be treated with an immediate or fast release cannabinoid receptor antagonist while a more mild antagonist is allowed to be released over an extended period of time. Further, different specific cannabinoid receptor antagonists at different dosage levels can be provided in a single tablet to provide the most effective method of treating drug addiction and drug addiction systems. Further, for nighttime use and for treating withdrawal symptoms specifically, a bilayer tablet providing the extended release of cannabinoids, along with a layer containing THC or melatonin and/or other sleep aids may be useful.

All publications mentioned above are hereby specifically incorporated herein by reference in full for the teachings for which they are cited. The examples and claims of the present invention are not limiting. Having read the present disclosure, those skilled in the art will readily recognize that numerous modifications, substitutions and variations can be made to the description without substantially deviating from the invention described herein. Such modifications, substitutions and variations constitute part of the invention described herein.

The invention claimed is:

1. A multi-layer composition comprising cannabinoids in both an immediate release layer and a sustained release layer, wherein the immediate release layer comprises:
   a) cannabinoid extract;
   b) dibasic calcium phosphate dehydrate
   c) pregelatinized modified starch;
   d) hydroxyethyl cellulose;
   e) purified water;
   f) homopolymers of acrylic acid;
   g) polyethylene oxide;
   h) hypromellose;
   i) methacrylic acid copolymer;
   j) magnesium stearate;
and wherein the sustained-release layer comprises:
   a) granules comprising
      i) beta-cyclodextrin
      ii) sesame oil;
      iii) cannabinoid resin;
      iv) glyceryl behenate;
      v) soy lecithin; and
      vi) peg-6 caprylic/capric glycerides; and
   b) extragranular excipients comprising:
      i) silica gel;
      ii) hydroxypropyl cellulose (HPC);
      iii) microcrystalline cellulose (MCC) and colloidal silicon dioxide (CSD); and
      iv) hydroxypropyl methylcellulose.

2. The multi-layer composition of claim 1 wherein the cannabinoid extract is an extract from *Cannabis sativa*.

3. The multi-layer composition of claim 1 wherein the extract comprises more than 90% cannabidiol, THC or THCV.

4. The multi-layer composition of claim 1 wherein the multi-layer tablet is in the form of a bi-layer tablet or a tri-layer tablet.

5. The multi-layer composition of claim 4 wherein the cannabinoid extract present in the immediate release layer comprises a therapeutically effective amount of natural or synthetic THC to promote onset of somnolence, and wherein the cannabinoid resin present in the sustained release layer comprises a therapeutically effective amount of a cannabinoid to provide for delayed release and to promote sleep.

6. The multi-layer composition according to claim 5 wherein the composition reduces the amount of lingering sleepiness that may be associated with the use of cannabinoids as sleep aids.

7. The multi-layer composition according to claim 6, wherein the composition comprises about twenty-five mg of cannabinoid resin per tablet.

8. The multi-layer composition according to claim 6, wherein the immediate-release layer further comprises at least one active ingredient for the improvement of sleep selected from the group consisting of: L-Theanine, Skullcap Herb (*Scutellaria lateriflora* L.), Rhodiola (*Rhodiola rosea* L.), and Chamomile Flower (*Matricaria Recutita*).

9. The multi-layer composition according to claim 1, wherein the multi-layer composition is in the form of a tablet.

10. The multi-layer composition according to claim 1, wherein the multi-layer composition is enclosed within a polymer barrier coat.

* * * * *